(12) United States Patent
Sussman et al.

(10) Patent No.: US 10,071,121 B2
(45) Date of Patent: Sep. 11, 2018

(54) CARDIAC, MESENCHYMAL AND ENDOTHELIAL PROGENITOR CELL (CPC) CHIMERAS AND METHODS FOR MAKING AND USING THEM

(71) Applicant: San Diego State University (SDSU) Foundation, San Diego, CA (US)

(72) Inventors: Mark A. Sussman, San Diego, CA (US); Pearl J. Quijada, San Diego, CA (US)

(73) Assignee: SAN DIEGO STATE UNIVERSITY (SDSU) FOUNDATION, San Diego, CA (US)

( * ) Notice: Subject to any disclaimer, the term of this patent is extended or adjusted under 35 U.S.C. 154(b) by 170 days.

(21) Appl. No.: 14/940,057

(22) Filed: Nov. 12, 2015

(65) Prior Publication Data

US 2016/0346330 A1  Dec. 1, 2016

Related U.S. Application Data

(60) Provisional application No. 62/080,110, filed on Nov. 14, 2014.

(51) Int. Cl.
| | |
|---|---|
| *A61K 35/28* | (2015.01) |
| *A61K 35/34* | (2015.01) |
| *A61K 35/44* | (2015.01) |
| *C12N 5/12* | (2006.01) |
| *C12N 5/16* | (2006.01) |
| *C12N 5/0775* | (2010.01) |
| *C12N 5/077* | (2010.01) |

(52) U.S. Cl.
CPC .............. *A61K 35/34* (2013.01); *A61K 35/28* (2013.01); *A61K 35/44* (2013.01); *C12N 5/0657* (2013.01); *C12N 5/0668* (2013.01); *C12N 5/16* (2013.01); *C12N 2510/00* (2013.01)

(58) Field of Classification Search
CPC ........ A61K 35/28; A61K 35/34; A61K 35/44; C12N 5/0657; C12N 5/0668; C12N 5/12; C12N 5/16; C12N 5/166
See application file for complete search history.

(56) References Cited

U.S. PATENT DOCUMENTS

| | | | | |
|---|---|---|---|---|
| 2006/0239983 A1* | 10/2006 | Anversa | ................ | A61K 35/34 424/93.7 |
| 2007/0253937 A1* | 11/2007 | Yoon | .................... | C12N 5/0663 424/93.7 |
| 2008/0213387 A1* | 9/2008 | Moore | ............... | G01N 33/5064 424/548 |

OTHER PUBLICATIONS

Spees et al, PNAS 100(5):2397-2402, 2003.*
Koyanagi et al, Circulation Res. 96:1039-1041, 2005.*
Katritsis et al, Catheterization and Cardiovascular Interventions 65:321-329, 2005.*
Metzele et al, FASEB J. 25:830-839, 2011.*

* cited by examiner

*Primary Examiner* — Kevin K Hill
(74) *Attorney, Agent, or Firm* — Greer, Burns & Crain; Gregory P. Einhorn

(57) ABSTRACT

In alternative embodiments, provided are chimeric cells, which in alternative embodiments are the so-called "cardiochimeras", and methods for making and using them. In alternative embodiments, exemplary chimeric cells as provided herein comprise a cardiac stem cell of cardiac origin or a cardiac progenitor cell fused to either a mesenchymal progenitor cell or mesenchymal stem cell, an endothelial progenitor cell or endothelial stem cell, or a cardiac stem cell or a cardiac progenitor cell. In alternative embodiments, the chimeric cells as provided herein comprise an endothelial progenitor cell, which may or may not be of cardiac origin, fused to either a mesenchymal progenitor cell or mesenchymal stem cell, an endothelial progenitor cell or endothelial stem cell, or a cardiac stem cell or a cardiac progenitor cell. In alternative embodiments, methods for making chimeric cells as provided herein further comprise selecting a cell fusion product comprising a viable chimera of the fused cells. In alternative embodiments, methods for making chimeric cells as provided herein comprise use of any known cell fusion technique, for example, using a Sendai virus, such as a Sendai virus Hemagglutinating Virus of Japan Envelope (HVJ-E), a polyethylene glycol, liposomes or lipids, a fusion protein, electrofusion and/or equivalents thereof. In alternative embodiments, provided are cell lines, chimera (chimeric) cell lines or chromosomally-stable chimera cell lines, derived or made from chimeric cells as provided herein. In alternative embodiments, provided are methods for inducing cardiogenesis in a mammalian heart comprising administration to an individual in need thereof (for example, a human), chimeric cells as provided herein, or a cell line, a chimera cell line or a chromosomally-stable chimera as provided herein. In alternative embodiments, provided are methods for treating or ameliorating a heart injury, a congenital or genetic heart defect, or a heart dysfunction, comprising administration to an individual in need thereof (for example, a human), chimeric cells as provided herein, or a cell line, a chimera cell line or a chromosomally-stable chimera as provided herein.

24 Claims, 26 Drawing Sheets
(24 of 26 Drawing Sheet(s) Filed in Color)
Specification includes a Sequence Listing.

Fig. 3

| hPGK | eGFP | mPGK | puro |
| hPGK | mKO | mPGK | puro |
| hPGK | mCherry | mPGK | bleo |

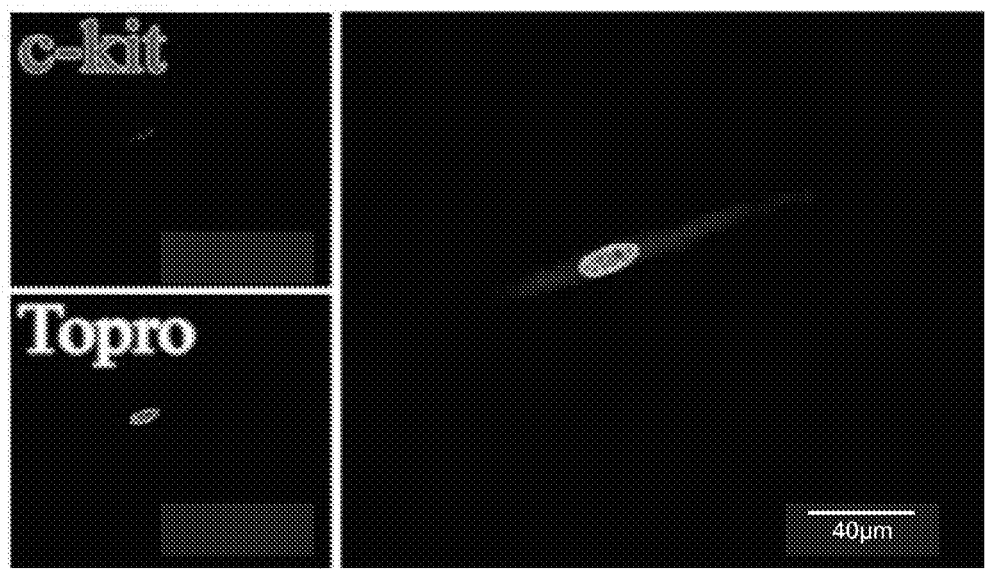
Fig. 4A(1)

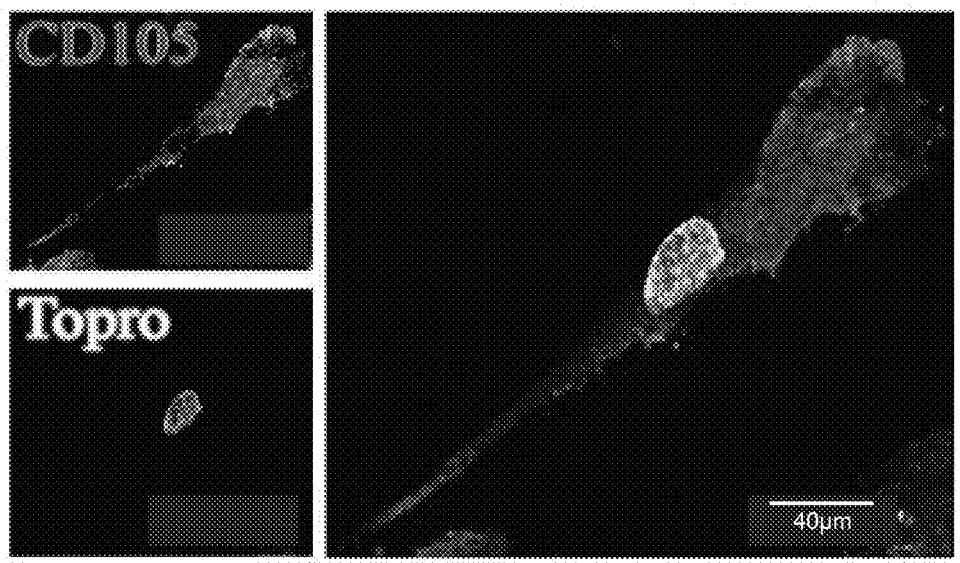
Fig. 4B(1)

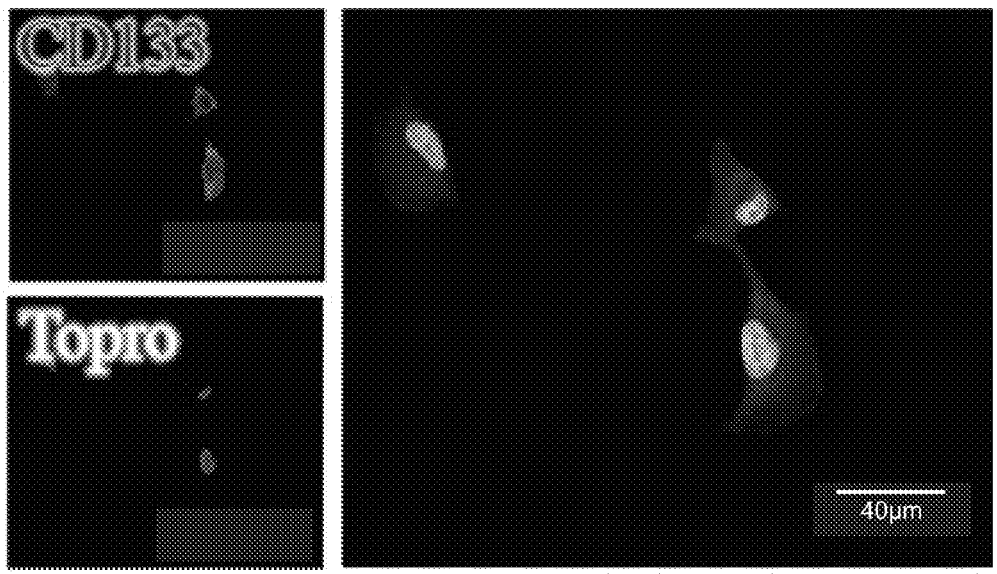
Fig. 4C(1)

Fig. 4 A(2).   Fig. 4 B(2).
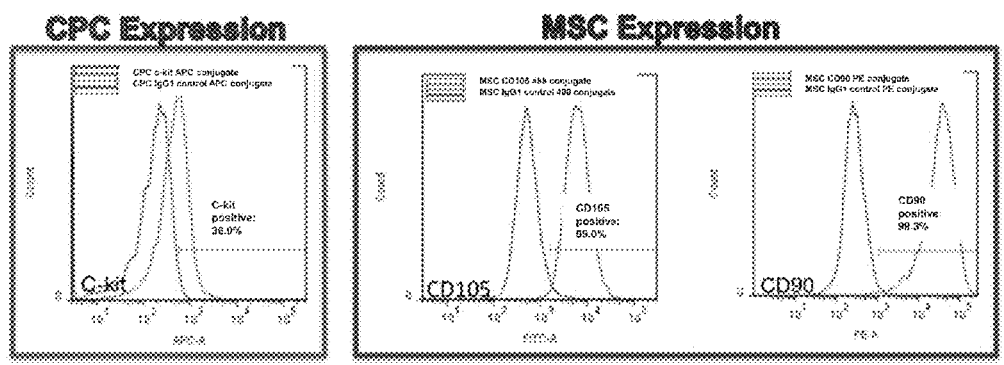
Fig. 4 C(2).
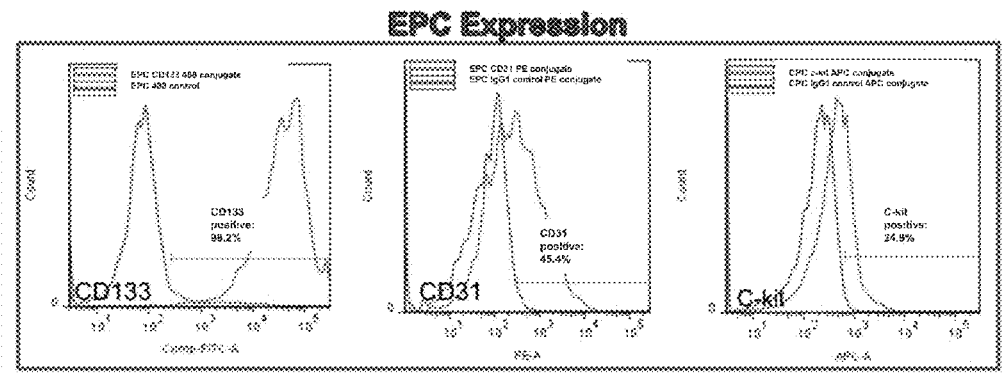

Fig. 5 A.  Fig. 5 B. 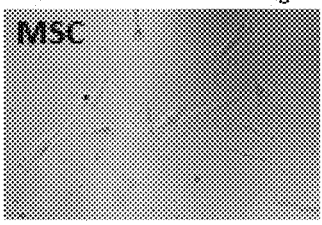 Fig. 5 C.
Fig. 5 D. 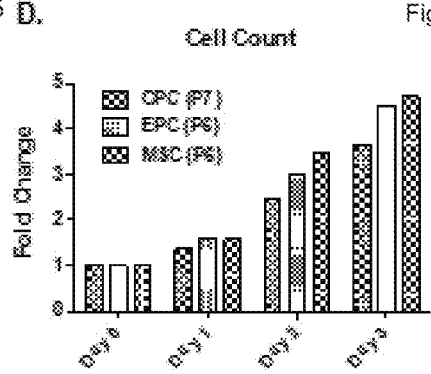 Fig. 5 E. 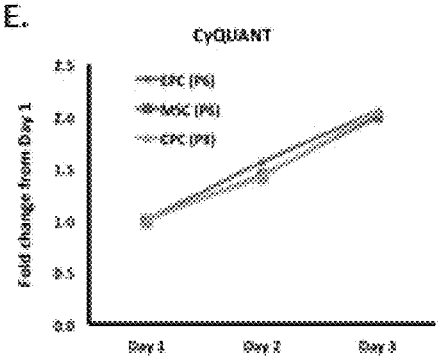

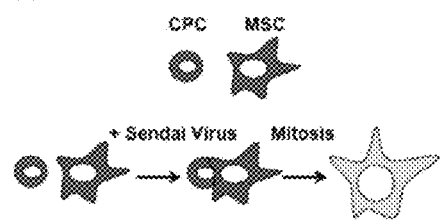
Fig. 9 A
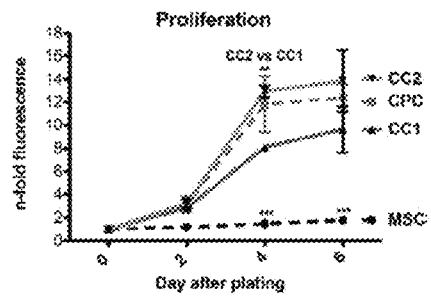
Fig. 9 B
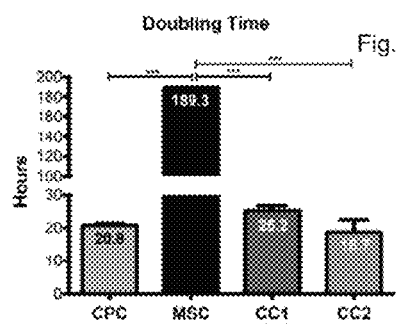
Fig. 9 C
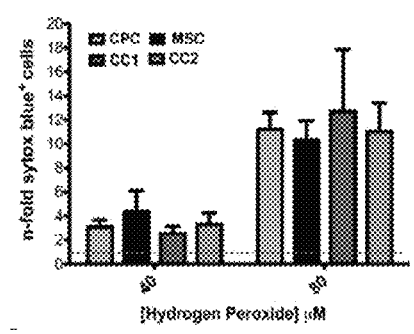
Fig. 9 D
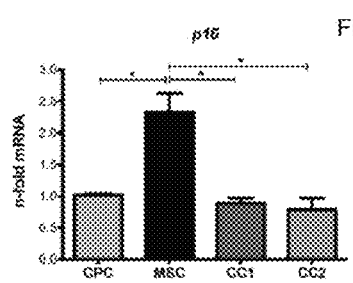
Fig. 9 E
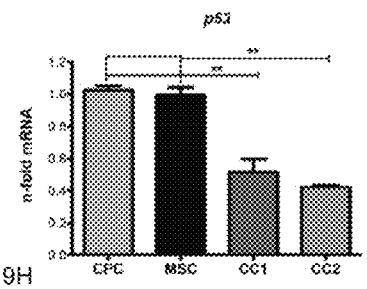
Fig. 9 F
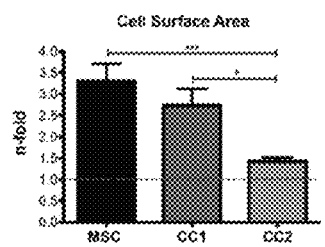
Fig. 9 G
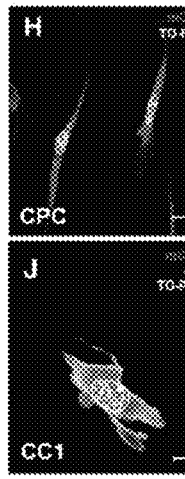
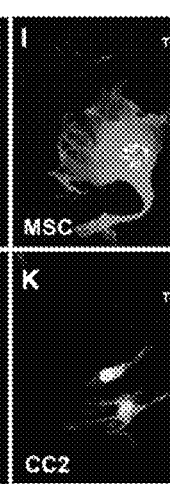
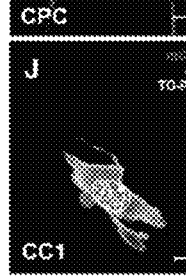
Fig. 9H
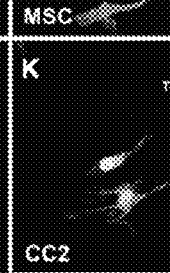
Fig. 9I
Fig. 9J
Fig. 9K Fig. 10A    Fig. 10C    Fig. 10E
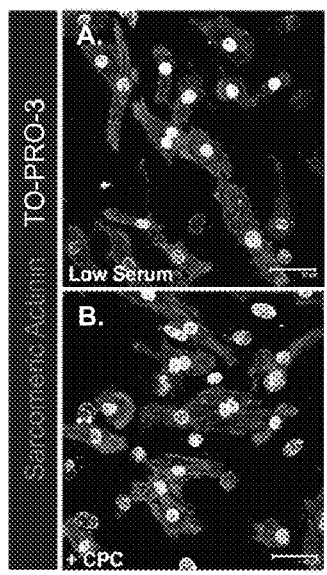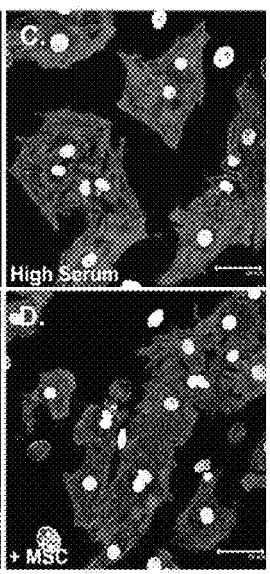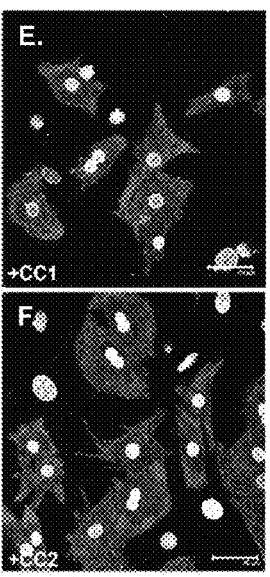
Fig. 10B    Fig. 10D    Fig. 10F
Fig. 10G.   Fig. 10H.
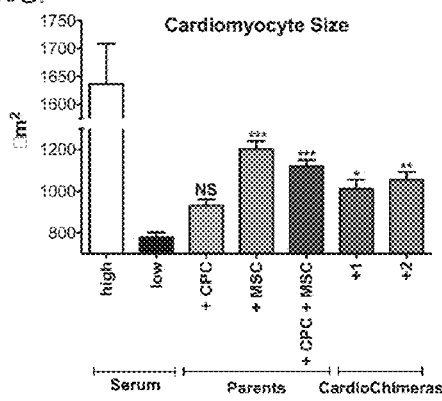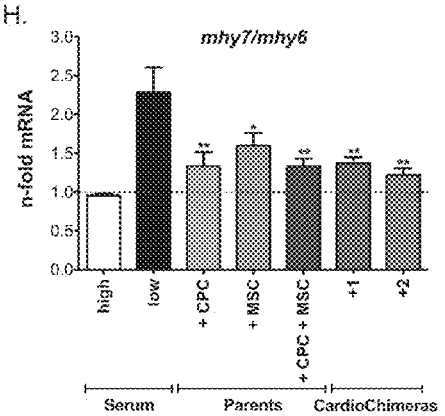
Fig. 10 I.   Fig. 10 J.
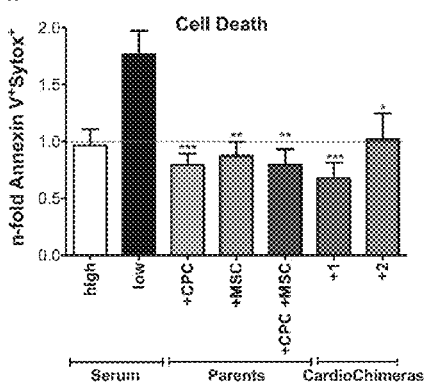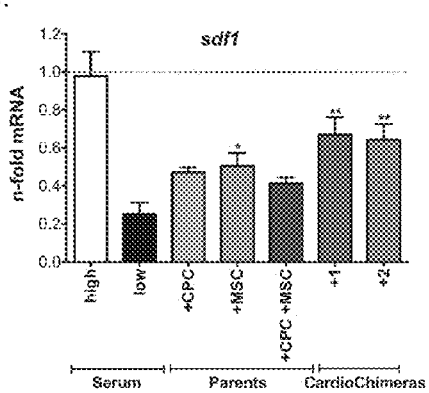

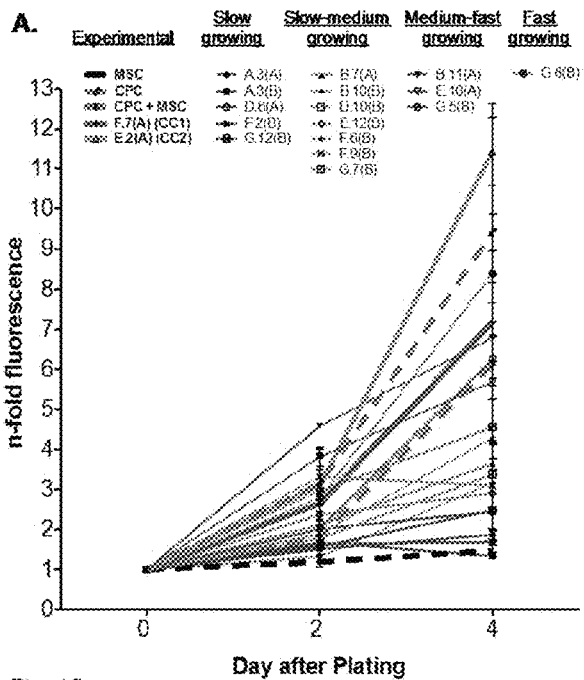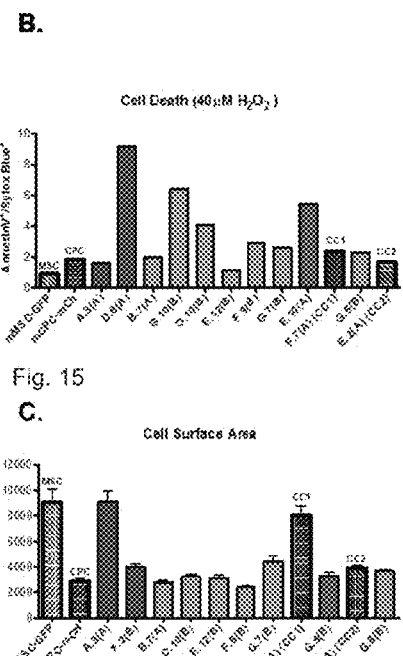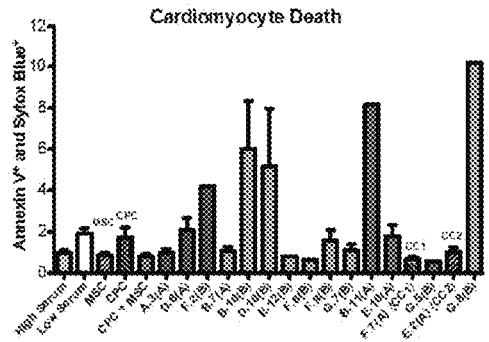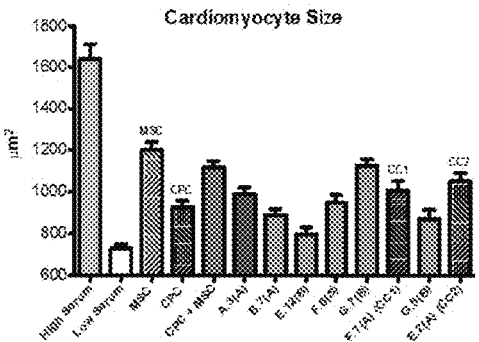
Fig. 15

Fig. 16
A.
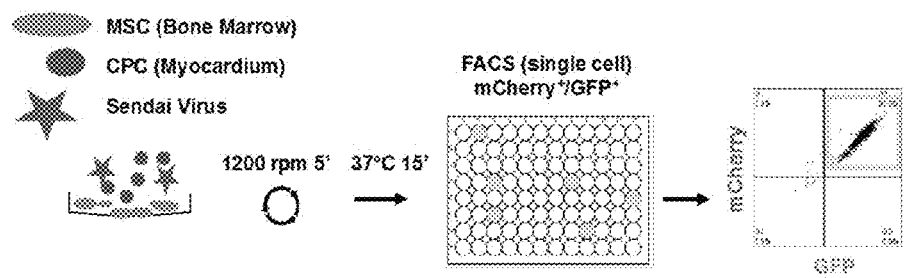
Fig. 16
B.
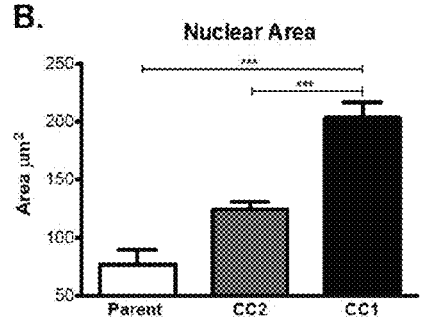
Fig. 16
C.
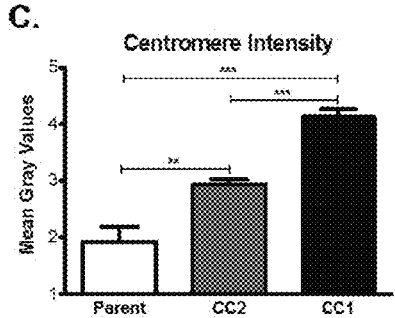
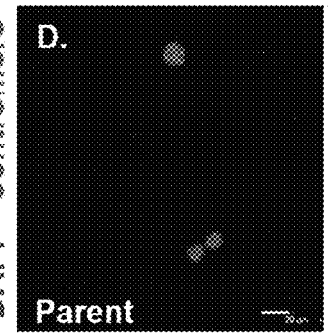
Fig. 16D
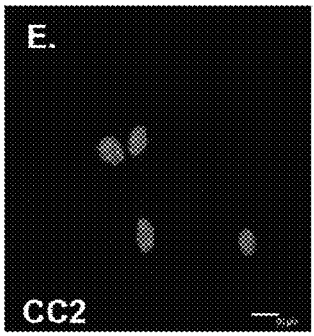
Fig. 16E
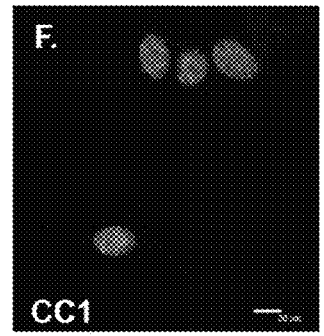
Fig. 16F

A.

B.

C.

D.

E.

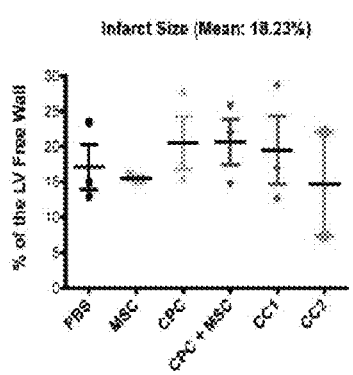
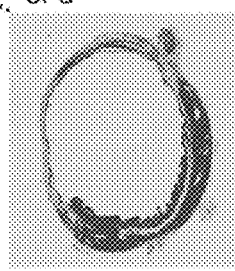
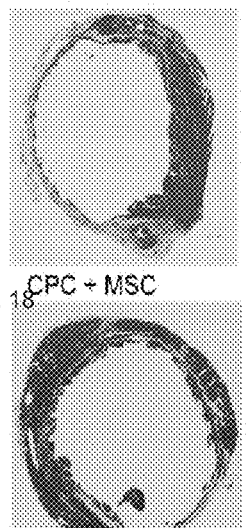
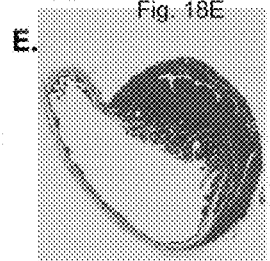
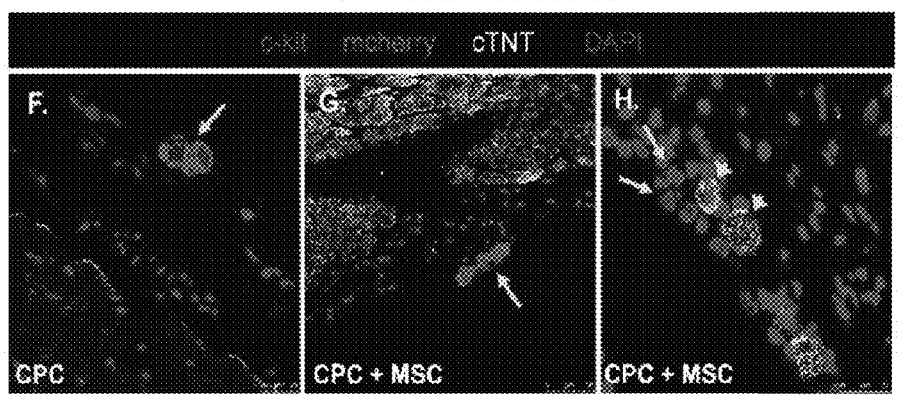
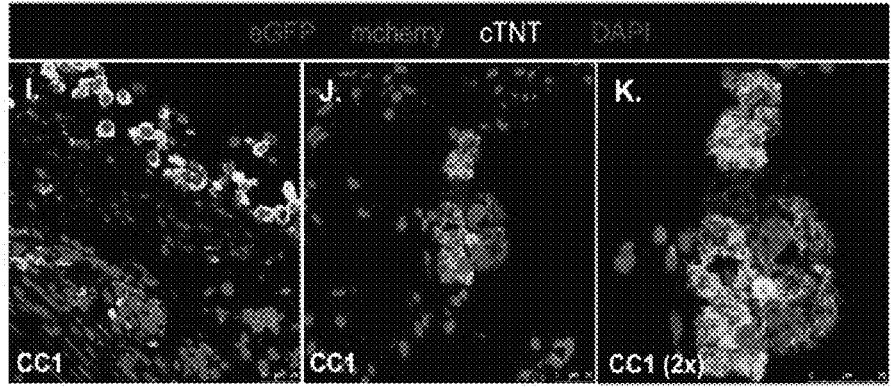
Fig. 18

FIG. 19A
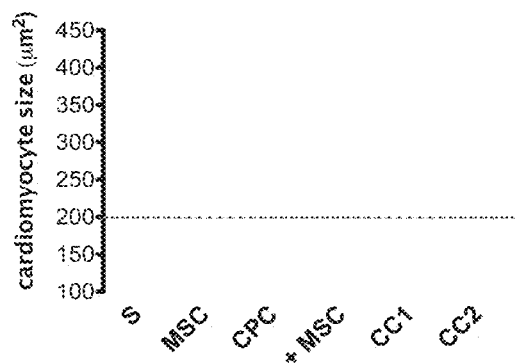
FIG. 19B  FIG. 19C  FIG. 19D
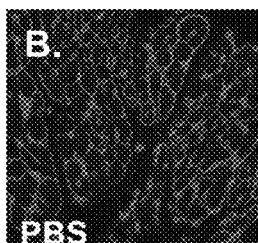 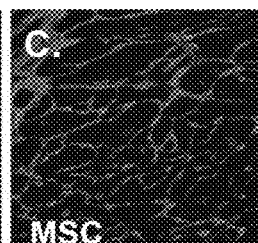 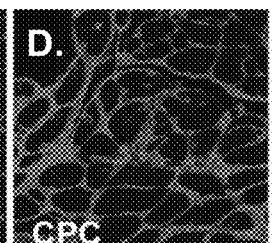
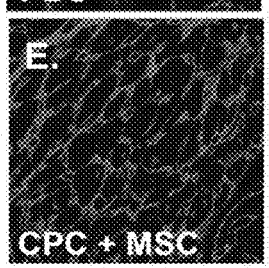 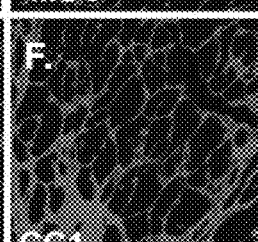 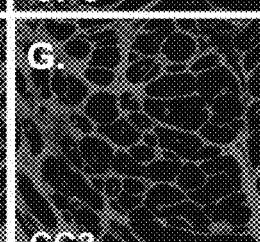
FIG. 19E  FIG. 19F  FIG. 19G

Fig. 20

| Growth Rate | Proliferation | | | Cell Death | | | Cell Surface Area/Morphology | | | Cardiomyocyte Growth | | | Cardiomyocyte Death | | | Exclusion Reason |
|---|---|---|---|---|---|---|---|---|---|---|---|---|---|---|---|---|
| | MSC | CPC | CPC+MSC | MSC | CPC | CPC+MSC | MSC | CPC | CPC+MSC | MSC | CPC | CPC+MSC | MSC | CPC | CPC+MSC | |
| slow growing | A.3(A) | A.3(A) | | A.3(A) | | | | | | | A.3(A) | | | | | very slow growing |
| | A.3(B) | | | | | | | | | | | | | | | did just grow/expand |
| | D.6(A) | D.6(A) | | | | | | | | D.6(A) | | | | | | poor cell survival |
| | F.2(B) | | | F.2(B) | | | F.2(B) | | | | | | | | | promoted cardiomyocyte death |
| | G.12(B) | | | | | | | | | | | | | | | very slow growing |
| slow-medium growing | B.7(A) | B.7(A) | | B.7(A) | | | B.7(A) | | | B.7(A) | | | | | | did not induce CM growth |
| | B.10(B) | B.10(B) | | D.10(B) | | | | | | | | | | | | poor cell survival and promoted cardiomyocyte death |
| | D.10(B) | D.10(B) | | D.10(B) | | | | | | | | | | | | poor cell survival and promoted cardiomyocyte death |
| | E.12(B) | E.12(B) | | E.12(B) | | | E.12(B) | | | E.12(B) | | | | | | did not induce CM growth |
| | F.6(B) | F.6(B) | | F.6(B) | | | F.6(B) | | | F.6(B) | | | | | | did not induce CM growth |
| | G.7(B) | G.7(B) | | G.7(B) | | | G.7(B) | | | G.7(B) | | | | | | Potential Cardio:Chimera Candidate |
| | F.9(B) | | | | | | | | | | | | | | | Potential Cardio:Chimera Candidate |
| medium-fast growing | B.11(A) | | | | | | | | | | | | | | | promoted cardiomyocyte death |
| | E.10(A) | E.10(A) | | | | | E.10(A) | | | | | | | | | poor cell survival |
| | F.7(A)(CC3) | F.7(A)(CC3) | | F.7(A)(CC3) | | | F.7(A)(CC3) | | | F.7(A)(CC3) | | | | | | Cardio:Chimera Candidate 1 |
| | G.5(B) | G.5(B) | | G.5(B) | | | G.5(B) | | | G.5(B) | | | | | | did not induce cardiomyocyte growth |
| fast growing | E.2(A)(CC2) | E.2(A)(CC2) | | E.2(A)(CC2) | | | E.2(A)(CC2) | | | E.2(A)(CC2) | | | | | | Cardio:Chimera Candidate 2 |
| | G.8(B) | | | G.8(B) | | | | | | | | | | | | promoted cardiomyocyte death |

Fig. 21

| Use: Flow Cytometry | Company | Primary Antibody Dilution | Secondary Antibody Dilution | Tyramide Amplification |
|---|---|---|---|---|
| Goat anti-CD117 (c-kit) | R&D Systems | 1:40 | Donkey anti-goat 647 (1:400) | N/A |
| Goat anti-IgG | Santa Cruz Biotechnology Inc. | 1:40 | Donkey anti-goat 647 (1:400) | N/A |
| Annexin V-APC | BD Biosciences | 1:40 | N/A | N/A |
| Sytox Blue | Life Technologies | 1:2000 | N/A | N/A |
| Use: Immuno-cytochemistry | Company | Primary Antibody Dilution | Secondary Antibody Dilution | Tyramide Amplification |
| Rat anti-mcherry | Life Technologies | 1:100 | Donkey anti-goat 555 (1:100) | N/A |
| Rabbit anti-GFP | Life Technologies | 1:100 | Donkay anti-goat 488 (1:100) | N/A |
| TO-PRO-3 iodide | Life Technologies | 1:10000 | N/A | N/A |
| Use: Immuno-histochemistry | Company | Primary Antibody Dilution | Secondary Antibody Dilution | Tyramide Amplification |
| Goat anti-CD117 (c-kit) | R&D Systems | 1:200 | Bovin anti-goat HRP (1:200) | Yes |
| Rat anti-mcherry | Life Technologies | 1:200 | Donkey anti-rat biotin (1:4500); Streptavidin HRP (1:100) | Yes |
| Rabbit anti-GFP | Life Technologies | 1:200 | Donkey anti-rabbit FITC (1:200); Sheep anti-FITC-HRP (1:400) | Yes |
| Mouse anti-cardiac troponin T | Thermo Scientific | 1:100 | Donkey anti-mouse 647 (1:100) | No |
| Isolectin-B$_4$-488 | Life Technologies | 1:100 | N/A | N/A |
| Wheat germ | Life Technolgies | 1:100 | N/A | N/A |

Fig. 22

| mRNA Primer | Forward | Reverse |
|---|---|---|
| Cardiac troponin T | 5'-ACCCTCAGGCTCAGGTTCA-3' (SEQ ID NO:1) | 5'-GTGTGCAGTCCCTGTTCAGA-3' (SEQ ID NO:2) |
| Connexin-43 | 5'-GGACCTTGTCCAGCAGCTT-3' (SEQ ID NO:3) | 5'-TCCAAGGAGTTCCACCACTT-3' (SEQ ID NO:4) |
| Smooth muscle 22 | 5'-GACTGCACTTCTCGGCTCAT-3' (SEQ ID NO:5) | 5'-CCGAAGCTACTCTCCTTCCA-3' (SEQ ID NO:6) |
| Platelet endothelial cell adhesion molecule | 5'-TGCTCTCGAAGCCCAGTATT-3' (SEQ ID NO:7) | 5'-TGTGAATGTTGCTGGGTCAT-3' (SEQ ID NO:8) |
| p53 | 5'-GCAGGGCTCACTCCAGCTACCT-3' (SEQ ID NO:9) | 5'-GTCAGTCTGAGTCAGGCCCCACT-3' (SEQ ID NO:10) |
| p16 | 5'-CGTACCCCGATTCAGGTGATG-3' (SEQ ID NO:11) | 5'-CGGGCGGGAGAAGGTAGT-3'; (SEQ ID NO:12) |
| Interleukin-6 | 5'-ATCCAGTTGCCTTCTTGGGACTGA-3' (SEQ ID NO:13) | 5'-TAAGCCTCCGACTTGTGAAGTGGT-3' (SEQ ID NO:14) |
| 18s | 5'-CGAGCCGCCTGGATACC-3' (SEQ ID NO:17) | 5'-CATGGCCTCAGTTCCGAAAA-3' (SEQ ID NO:16) |

SEQUENCE LISTING

<160> NUMBER OF SEQ ID NOS: 1

<210> SEQ ID NO 1
<211> LENGTH: 17
<212> TYPE: DNA
<213> ORGANISM: artificial sequence
<220> FEATURE:
<223> OTHER INFORMATION: synthetic oligonucleotide

<400> SEQUENCE: 1
attcgttgga aacggga                                                    17

CARDIAC, MESENCHYMAL AND ENDOTHELIAL PROGENITOR CELL (CPC) CHIMERAS AND METHODS FOR MAKING AND USING THEM

RELATED APPLICATIONS

This U.S. utility patent application claims benefit of priority under 35 U.S.C. § 119(e) of U.S. provisional patent application Ser. No. 62/080,110, filed Nov. 14, 2014. The aforementioned application is expressly incorporated herein by reference in its entirety and for all purposes.

STATEMENT AS TO FEDERALLY SPONSORED RESEARCH

This invention was made with government support under grant numbers NIH F31HL117623, R01HL067245, R37HL091102, R01HL105759, R01HL113656, R01HL113647, R01HL122525, awarded by the National Institute of General Medical, National Institutes of Health (NIH), DHHS. The government has certain rights in the invention.

TECHNICAL FIELD

This invention generally relates to cell and molecular and stem cell biology and regenerative medicine. In alternative embodiments, provided are chimeric cells, which in alternative embodiments are the so-called "cardiochimeras", and methods for making and using them. In alternative embodiments, the chimeric cells as provided herein comprise a cardiac stem cell of cardiac origin or a cardiac progenitor cell fused to either a mesenchymal progenitor cell or mesenchymal stem cell, an endothelial progenitor cell or endothelial stem cell, or a cardiac stem cell or a cardiac progenitor cell. In alternative embodiments, chimeric cells as provided herein comprise an endothelial progenitor cell, which may or may not be of cardiac origin, fused to either a mesenchymal progenitor cell or mesenchymal stem cell, an endothelial progenitor cell or endothelial stem cell, or a cardiac stem cell or a cardiac progenitor cell. In alternative embodiments, methods for making chimeric cells as provided herein further comprise selecting a cell fusion product comprising a viable chimera of the fused cells. In alternative embodiments, methods for making chimeric cells as provided herein comprise use of any known cell fusion technique, for example, using a Sendai virus, such as a Sendai virus Hemagglutinating Virus of Japan Envelope (HVJ-E), a polyethylene glycol, liposomes or lipids, a fusion protein, electrofusion and/or equivalents thereof. In alternative embodiments, provided are cell lines, chimera (chimeric) cell lines or chromosomally-stable chimera cell lines, derived or made from chimeric cells as provided herein. In alternative embodiments, provided are methods for inducing cardiogenesis in a mammalian heart comprising administration to an individual in need thereof (for example, a human), chimeric cells as provided herein, or a cell line, a chimera cell line or a chromosomally-stable chimera as provided herein. In alternative embodiments, provided are methods for treating or ameliorating a heart injury, a congenital or genetic heart defect, or a heart dysfunction, comprising administration to an individual in need thereof (for example, a human), chimeric cells as provided herein, or a cell line, a chimera cell line or a chromosomally-stable chimera as provided herein.

BACKGROUND

Cellular therapy using stem cells derived from the bone marrow and cardiac origin are validated to treat damage after myocardial infarction (MI) in both small animal models and human clinical trials. The use of cellular therapy to treat MI has been largely unsatisfactory, with many protocols showing little to no improvement in cardiac function after long-term follow up studies. The inherent limitation of autologous stem cell therapy is that cells derived from aged organs have increased expression of senescent markers and acquisition of chromosomal abnormalities leading to undesirable cellular characteristics such as slowed proliferation and increased susceptibility to cellular death. Furthermore, based on animal models, cellular survival and engraftment is hindered by adverse inflammation, inhibiting the ability of transplanted stem cells to efficiently differentiate into cardiac cells. Improvement of stem cell engraftment and survival has been attempted by co-injection of stem cells with biomaterials, cytokines and growth factors, or by genetically enhancing cells with pro-survival and anti-apoptotic genes.

The heart is capable of limited regeneration, as evidenced by cardiomyocyte re-entry into the cell cycle and production of new mono-nucleated myocytes during aging and after pathological damage. New myocyte formation is partially due to reserve c-kit$^+$ cardiac progenitor cells (CPCs) found in complex microenvironments or niches. In vivo, CPCs retain expression of primitive cardiac transcription factors and upon activation can give rise to cells of the cardiac lineages.

The regenerative potential of stem cells in a clinical setting is still largely unrecognized. Although stem cells are suggested to function through a variety of mechanisms for myocardial repair, in practice stem cells have been inherently limited because of origin and potency status.

SUMMARY

In alternative embodiments, provided are methods for making a chimeric cell, comprising: (a) (i) providing a first cell, wherein the first cell comprises: (1) a cardiac stem cell of cardiac origin; (2) a cardiac progenitor cell (CPC), optionally a human c-kit$^+$ CPC; or, (3) an endothelial progenitor cell; (ii) providing a second cell, wherein the second cell comprises: (1) a mesenchymal progenitor cell or mesenchymal stem cell; (2) an endothelial progenitor cell or endothelial stem cell; or (3) a cardiac stem cell or a cardiac progenitor cell; and, (iii) inducing fusion between the first cell and the second cell, thereby generating a cell fusion product; or (b) the method of (a), further comprising selecting a cell fusion product comprising a viable chimera of the first and the second cell.

In alternative embodiments, methods further comprise clonally expanding the viable chimera, and optionally further comprising selecting a substantially chromosomally-stable chimera cell line from the clonally expanded chimera, and optionally wherein multiple said chimeras are produced, further comprising selecting a chimera cell line therefrom on the basis of enhanced cardiogenic potential, reduced immunogenic potential, or both enhanced cardiogenic potential and reduced immunogenic potential.

In alternative embodiments, the fusion is induced using a method comprising use of a cell fusion technique selected from the group consisting of: a Sendai virus, optionally a Sendai virus Hemagglutinating Virus of Japan Envelope (HVJ-E); a polyethylene glycol; liposomes or lipids; a fusion protein; and electrofusion.

In alternative embodiments, the second cell is an endothelial progenitor cell or stem cell; or, a mesenchymal progenitor cell or stem cell. In alternative embodiments, the second cell is of cardiac origin, or is of non-cardiac origin. In alternative embodiments, the second cell is a cardiac stem cell of cardiac origin, a cardiac progenitor cell, a mesenchymal stem cell, or an endothelial progenitor cell. In alternative embodiments, the first cell is a cardiac progenitor cell and the second cell is a mesenchymal stem cell. In alternative embodiments, the first cell is a cardiac progenitor cell and the second cell is a mesenchymal stem cell. In alternative embodiments, the first cell is an endothelial progenitor cell and the second cell is a mesenchymal stem cell. In alternative embodiments, the first cell is an endothelial progenitor cell and the second cell is a cardiac progenitor cell.

In alternative embodiments, the cell is a human or a non-human cell, optionally a mammalian cell, optionally a murine cell; wherein optionally a cell fusion is a human cell to human cell fusion, a human cell to non-human cell fusion, or a non-human cell to a non-human cell fusion, optionally a human-murine (e.g., rodent, rat, mouse) cell fusion product, or a murine to murine cell fusion product.

In alternative embodiments, provided are cardiochimeras, a cell fusion product or a viable chimera, produced by a method as provided herein.

In alternative embodiments, provided are a cell line, a chimera cell line or a chromosomally-stable chimera cell line, produced by a method as provided herein, or produced from or derived from a cardiochimera, a cell fusion product or a viable chimera as provided herein.

In alternative embodiments, provided are a cardiochimera, a cell fusion product or a viable chimera, comprising: a fusion product of: (a) a first cell comprising: (1) a cardiac stem cell of cardiac origin; (2) a cardiac progenitor cell (CPC), optionally a human c-kit$^+$ CPC; or, (3) an endothelial progenitor cell; and, (b) a second cell comprising a stem cell or a progenitor cell, wherein optionally the first cell is of cardiac origin, and optionally the second cell comprises a cardiac stem cell, a mesenchymal stem cell or an endothelial progenitor cell, and optionally the second stem cell is of cardiac origin or non-cardiac origin, and optionally the cell is a human or a non-human cell, optionally a mammalian cell, optionally a murine cell; wherein optionally the cardiochimera, cell fusion product or viable chimera cell is the product of a human cell to human cell fusion, a human cell to non-human cell fusion, or a non-human cell to a non-human cell fusion, optionally a human-murine (e.g., rodent, rat, mouse) cell fusion product, or a murine to murine cell fusion product.

In alternative embodiments, for a cardiochimera, a cell fusion product or a viable chimera as provided herein, a second cell comprises: (a) a mesenchymal stem cell of cardiac origin or non-cardiac origin; (b) an endothelial progenitor cell of cardiac origin or non-cardiac origin; or (c) a cardiac stem cell or a cardiac progenitor cell. In alternative embodiments, the second cell is a cardiac stem cell of cardiac origin and is a cardiac progenitor cell, a mesenchymal stem cell, or an endothelial progenitor cell. In alternative embodiments, the first cell is a cardiac progenitor cell and the second cell is a mesenchymal stem cell. In alternative embodiments, the first cell is a cardiac progenitor cell and the second cell is a mesenchymal stem cell. In alternative embodiments, the first cell is an endothelial progenitor cell and the second cell is a mesenchymal stem cell. In alternative embodiments, the first cell is an endothelial progenitor cell and the second cell is a cardiac progenitor cell. In alternative embodiments, the first cell, the second cell, or the first cell and the second cell, are human cells.

In alternative embodiments, provided are products of manufacture comprising: (a) a chimeric cell made by a method as provided herein, (b) a cardiochimera, a cell fusion product or a viable chimera as provided herein, (c) a cell line, a chimera cell line or a chromosomally-stable chimera as provided herein; or (e) any combination thereof, wherein optionally the product of manufacture comprises a drug delivery device, an implant, a catheter, a stent, or a medical device, wherein optionally the chimeric cell or chimeric cells are formulated with or mixed with or within a gel, a hydrogel, a chitosan-based hydrogel, a biocompatible scaffold, or a biomimetic support.

In alternative embodiments, provided are methods for inducing cardiogenesis in a mammalian heart, comprising: (a) providing a cell or a plurality of cells, or product of manufacture, selected from the group consisting of: (1) a chimeric cell made by a method as provided herein, (2) a cell line, a chimera cell line or a chromosomally-stable chimera as provided herein; (3) a cell line, a chimera cell line or a chromosomally-stable chimera as provided herein; (4) a cardiochimera, a cell fusion product or a viable chimera of any o as provided herein, (5) a product of manufacture as provided herein; and (6) any combination thereof; (b) introducing the cell or cells of (a), or product of manufacture, into or on or approximate to, a mammalian heart, thereby inducing cardiogenesis in the mammalian heart.

In alternative embodiments of the methods, the mammalian heart has an injury, a congenital or genetic defect, or a dysfunction, and the method is effective to treat the injury, defect or the dysfunction, wherein optionally the injury, defect or dysfunction is a myocardial infarction (MI), an ischemic injury, a heart failure, or results from a myocardial infarction (MI).

In alternative embodiments, provided are methods for treating or ameliorating a heart injury, an injury subsequent to a myocardial infarction (MI), a congenital or genetic heart defect, or a heart dysfunction, comprising: (a) providing a cell or a plurality of cells, or product of manufacture, selected from the group consisting of: (1) a chimeric cell made by a method as provided herein, (2) a cell line, a chimera cell line or a chromosomally-stable chimera as provided herein; (3) a cell line, a chimera cell line or a chromosomally-stable chimera as provided herein; (4) a cardiochimera, a cell fusion product or a viable chimera as provided herein, (5) a product of manufacture as provided herein; and (6) any combination thereof; (b) introducing, administering or applying the cell or cells or product of manufacture of (a) into a heart of an individual, or to the individual, in need thereof, thereby treating or ameliorating the heart injury, the injury subsequent to a myocardial infarction (MI), congenital or genetic heart defect, or heart dysfunction or heart failure.

In alternative embodiments of the methods, the chimeric cell or chimeric cells are administered with or formulated with or mixed with a gel, a hydrogel, a chitosan-based hydrogel, a biocompatible scaffold, or a biomimetic support.

In alternative embodiments, provided are uses of a chimeric cell as provided herein, or provided are uses of a cell or cells, or product of manufacture, selected from the group consisting of: (a) providing a cell or a plurality of cells, or product of manufacture, selected from the group consisting of: (1) a chimeric cell made by a method as provided herein, (2) a cell line, a chimera cell line or a chromosomally-stable chimera as provided herein; (3) a cell line, a chimera cell line or a chromosomally-stable chimera as provided herein; (4)

a cardiochimera, a cell fusion product or a viable chimera as provided herein, (5) a product of manufacture as provided herein; and (6) any combination thereof;

for treating or ameliorating an injury subsequent to a myocardial infarction (MI), a heart injury, a congenital or a genetic heart defect, or a heart dysfunction or heart failure.

The details of one or more embodiments as provided herein are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The drawings set forth herein are illustrative of embodiments as provided herein and are not meant to limit the scope of the invention as encompassed by the claims.

FIG. 3 schematically illustrates three exemplary lentiviral constructs used to label and identify stem cells in vitro and in vivo, as described in detail in Example 1, below.

FIG. 4A(1) and FIG. 4A(2), FIG. 4B(1) and FIG. 4B(2) and FIG. 4C(1) and FIG. 4C(2) illustrate images of the surface characterization of cardiac derived stem cells, and graphically illustrates data therefrom: FIG. 4A(1) and FIG. 4A(2); CPCs express c-kit, FIG. 4B(1) and FIG. 4B(2); MSCs express CD105 and CD90, and FIG. 4C(1) and FIG. 4C(2) EPCs express CD133, CD31, as described in detail in Example 1, below.

FIG. 5A, FIG. 5B, FIG. 5C illustrate light microscopy images of the phenotypic characteristics of cardiac derived stem cells (representative images of CPCs in FIG. 5A, MSCs in FIG. 5B, and EPCs in FIG. 5C); and FIG. 5E and FIG. 5E graphically illustrate data therefrom using cell counting (FIG. 5D) and a CyQuant assay (FIG. 5E), as described in detail in Example 1, below.

FIG. 6A, FIG. 6B and FIG. 6C illustrate images of the characterization of c-kit$^+$ CPCs and MSCs, and graphically illustrates the results therefrom: FIG. 6A illustrates CPCs expressing mCherry and FIG. 6B illustrates MSCs expressing GFP as determined by immunofluorescence. TO-PRO-3 stain was used to label nuclei, and FIG. 6C illustrates proliferation rates of non-infected and transduced CPCs and MSCs as measured by cyquant assay and represented as a fold change fluorescence compared to day of plating, as described in detail in Example 1, below.

FIG. 7A illustrates a representative image of a stem cell hybrid derived after fusion of mouse c-kit$^+$ CPCs with MSCs; and FIG. 7B illustrates proliferation rates of CPC-MSC hybrids as quantitated by CyQuant assay and represented as a fold change fluorescence compared to day of plating relative to parental cells expressing mCh or GFP alone, as described in detail in Example 1, below.

FIG. 8A illustrates relative cell surface area; FIG. 8B illustrates cell length to width ratio; FIG. 8C illustrates cell roundness was measured in hybrids compared to parental cell lines; FIG. 8D illustrates representative images of four stem cell hybrids using light microscopy, as described in detail in Example 1, below.

FIG. 9A-K illustrates Phenotypic Characterization of CardioChimeras: FIG. 9(A) Schematic representation of the creation of CardioChimeras; FIG. 9(B) Proliferation of CCs, CPCs and MSCs represented as a fold change relative to day of plating; FIG. 9(C) Cell doubling time in hours; FIG. 9(D) Cell death assay of CCs and parents cells after treatment with 40 μM or 80 μM hydrogen peroxide represented as a fold change relative to cells not treated with hydrogen peroxide; FIG. 9(E) p16 and FIG. 9(F) p53 gene expression normalized to ribosomal 18s and represented as a fold change relative to CPCs; FIG. 9(G) Cell surface area represented as a fold change normalized to CPCs (blue dashed line, 1.0); Fluorescent images of FIG. 9(H) CPCs; FIG. 9(I) MSCs; FIG. 9(J) CC1 or FIG. 9(K) CC2, as described in detail in Example 2, below.

FIG. 10A-O illustrates that CardioChimeras promote cell growth and have increased commitment and paracrine gene expression after in vitro co-culture with cardiomyocytes: FIG. 10(A) NRCMs in low serum; FIG. 10(B) NRCMS in high serum; FIG. 10(C) NRCMs in low serum and after the addition of MSCs; FIG. 10(D) CC1; FIG. 10(E) CC2 or FIG. 10(F) CPCs for 24 hours; cardiomyocytes also were visualized by staining with sarcomeric actinin, and TO-PRO-3 iodide was used to visualize nuclei: FIG. 10(G) Quantitation of cardiomyocyte size; FIG. 10(H) Gene expression of mhy7 over mhy6 represented as a fold change relative to high serum; FIG. 10(I) Cardiomyocyte cell death; FIG. 10(J) sdf-1 gene expression in cardiomyocytes alone after the addition of stem cells; FIG. 10K, FIG. 10L, FIG. 10M graphically illustrate Gene expression in stem cells after a 7-day co-culture with NRCMs; FIG. 10(K) sm22 FIG. 10(L) pecam gene expression; FIG. 10M and FIG. 10N graphically illustrate il6 gene expression analyzed in stem cells after a 24-hour co-culture with NRCMs; FIG. 10(O) IL-6 expression confirmed by ELISA, as described in detail in Example 2, below.

FIG. 11A-N illustrates that CardioChimeras improve left ventricular wall structure and cardiac function after myocardial injury: FIG. 11(A) Longitudinal assessment of anterior wall thickness during systole (mm) over 18 weeks; FIG. 11(B) Heart weight to body weight ratio (mg/g) at 12 WPI; FIG. 11(C) 18 WPI, sample sizes of 3-5 mice per group; FIG. 11(D) Longitudinal assessment of ejection fraction (%); FIG. 11(E) Positive and FIG. 11(F) graphically illustrate negative developed pressure over time represented as mmHg/sec at 4, 12 and 18 WPI; FIG. 11(G) graphically illustrates change in infarct size between 4 and 12 weeks time points; FIG. 11H, FIG. 11I, FIG. 11J, FIG. 11K, FIG. 11L, FIG. 11M, and FIG. 11N illustrates a Masson's Trichrome staining and representative images of infarct size and fibrosis in FIG. 11(H) Sham, FIG. 11(I) PBS, FIG. 11(J) MSC, FIG. 11(K) CPC, FIG. 11(L) CPC+MSC, FIG. 11(M) CC1 and FIG. 11(N) CC2, as described in detail in Example 2, below.

FIG. 12A-O illustrates that CardioChimeras have increased engraftment, expression of cardiomyogenic markers and support the increased presence of c-kit$^+$ cells in the myocardium 12 weeks after damage: FIG. 12(A) graphically illustrates the number of c-kit$^+$ cells over the area of left ventricular free wall (mm$^2$) in a 4-week damaged heart; representative whole heart scans are illustrated in FIG. 12(B) illustrates CPC+MSC and FIG. 12(C) illustrates CC2 treated hearts to visualize c-kit$^+$ cells (red); FIG. 12(B) and FIG. 12(C) illustrates C-kit$^+$ cells which are identified by yellow arrows; FIG. 12(D) graphically illustrates the number of c-kit$^+$ cells in 12-week damaged heart, and representative whole heart scans are illustrated in FIG. 12(E) CPC+MSC, FIG. 12(F) CC1 and FIG. 12(G) CC2 treated hearts to visualize exogenous mcherry$^+$ cells (green) and c-kit$^+$ cells (red); FIG. 12(E), FIG. 12(F) and FIG. 12(G) illustrates C-kit$^+$ cells identified by yellow arrows; FIG. 12(H) graphically illustrate cell engraftment efficiency (%); FIG. 12(I) illustrates MSC detected by GFP fluorescence at 12 weeks; FIG. 12(J) illustrates a 2× zoom of a MSC in the border zone area; FIG. 12(K) illustrates C-kit$^+$/mcherry$^+$ CPCs in the border zone area; FIG. 12(L) illustrates Mcherry$^+$ CPC in CPC+MSC treated heart; FIG. 12(M) illustrates Mcherry$^+$ CC1 visualized in the infarcted area surrounded by c-kit$^+$ cells (green); FIG. 12(M) illustrates an Overlay of cTNT (exogenous-cTNT, yellow) in CC1 mcherry labeled cells; FIG. 12(N) illustrates Mcherry$^+$ CC2 visualized in the infarcted area surrounded by c-kit$^+$ cells (green); FIG. 12(O) illustrates Mcherry$^+$ CC2 (red) visualized in the infarcted area surrounded by c-kit$^+$ cells (green); FIG. 12(O) illustrates an Overlay of cTNT (exogenous-cTNT, yellow) in CC2 mcherry labeled cells, as described in detail in Example 2, below.

FIG. 13A-N illustrates that CardioChimeras increase capillary density in the infarct area: FIG. 13(A) graphically illustrates capillary density in the border zone and FIG. 13(B) graphically illustrates Infarcted heart regions; FIG. 13C, FIG. 13D, FIG. 13E, FIG. 13F, FIG. 13G, FIG. 13H and FIG. 13I illustrate representative border zone images to visualize isolectin$^+$ structures;

FIG. 13J, FIG. 13K, FIG. 13L, FIG. 13M, FIG. 13N, FIG. 13N', FIG. 13O and FIG. 13O' illustrate representative infarct zone images to visualize and quantitate isolectin$^+$ structure, as described in detail in Example 2, below.

FIG. 14A-L illustrates that CPC, MSC and CardioChimera treatment antagonizes cardiomyocyte hypertrophy in the remote region and preserves cardiomyocyte size in the infarcted regions; FIG. 14(A) graphically illustrates mean cardiomyocyte size in the remote and FIG. 14(B) graphically illustrates Infarct regions; FIG. 14C, FIG. 14D, FIG. 14E, FIG. 14F, FIG. 14G, FIG. 14H and FIG. 14I illustrates representative images of remote area cardiomyocyte size;

FIG. 14J, FIG. 14K, FIG. 14L, FIG. 14M, FIG. 14N and FIG. 14O illustrate representative images of infarct area cardiomyocytes, as described in detail in Example 2, below.

FIG. 15A-15E graphically illustrates Phenotypic Characterization of CardioChimera clones: FIG. 15(A) Proliferation data for the 18 CardioChimera clones relative to day of plating using a direct-fluorescent based assay (CyQuant Assay); FIG. 15(B) CardioChimera death after treatment with hydrogen peroxide stimulus; FIG. 15(C) Neonatal rat cardiomyocytes incubated in high or low serum or with the addition of parent cells, parent cells combined or CardioChimeras; FIG. 15(D) Cell death was quantitated by measuring a fold change of Annexin V$^+$ and Sytox Blue$^+$ cardiomyocytes relative to cardiomyocytes in high serum; FIG. 15(E) Cardiomyocyte size was quantitated in high serum or with the addition parent cells, parent cells combined or CardioChimeras, as described in detail in Example 2, below.

FIG. 16A-F illustrates that CardioChimeras have increased nuclear size and DNA content; FIG. 16(A) schematically illustrates a detailed protocol for the fusion and clonal expansion of CardioChimeras; FIG. 16(B) graphically illustrates measurement of nuclear size and FIG. 16(C) graphically illustrates centromere intensity in parent MSCs, CC2 and CC1; FIG. 16(D) illustrates representative images of nuclei in parent FIG. 16(E) CC2 and FIG. 16(F) CC1, as described in detail in Example 2, below.

FIG. 17(A)C-kit protein expression as analyzed by flow cytometry; FIG. 17(B) connexin 43, FIG. 17(C) pecam (cd31), FIG. 17(D) sm22 and FIG. 17(E) cTNT (tnnt3) gene expression was analyzed by qRT-PCR in CPC, MSC, CPC+MSC, CC1 and CC2 after normalization to ribosomal 18s, as described in detail in Example 2, below.

FIG. 18A-K illustrates Cellular Engraftment of CardioChimeras 4 weeks after damage; FIG. 18(A) graphically illustrates that infarct size was not significantly different between infarcted groups; FIG. 18B, FIG. 18C, FIG. 18D and FIG. 18E illustrate Masson's Trichrome staining and representative images of FIG. 18(B) PBS, FIG. 18(C) CPC, FIG. 18(D) CPC+MSC and FIG. 18(E) CC1 hearts to visualize scar size and fibrosis; FIG. 18(F) Mcherry$^+$ CPCs detected in the infarct area in CPC treated hearts; FIG. 18(G) Mcherry$^+$ CPCs detected in the infarct area in CPC+MSC treated hearts; FIG. 18(H) Mcherry$^+$ CPCs adjacent to c-kit$^+$/cTNT$^+$ cardiomyocytes in CPC+MSC treated hearts; FIG. 18(I) and FIG. 18(J) CC1 expressing eGFP and mcherry in the infarcted area; FIG. 18(K) 2× zoom of CC1, as described in detail in Example 2, below.

FIG. 19A-G illustrates Cardiomyocyte size is unaffected in the border zone region after treatment; FIG. 19(A) graphically illustrates Mean cardiomyocyte size in the border zone regions; FIG. 19B, FIG. 19C, FIG. 19D, FIG. 19E, FIG. 19F and FIG. 19G illustrates representative images of border zone area cardiomyocytes, as described in detail in Example 2, below.

FIG. 20 illustrates Table I: Phenotypic characterization of 18 exemplary CardioChimeras; Individual clones were analyzed for phenotypic properties such as proliferation, cell death and cell surface area and potential for paracrine mediated effects on cardiomyocytes, e.g., cardiomyocyte growth and cardiomyocyte Death; the last panel specifies exclusion reason(s), as described in detail in Example 2, below.

FIG. 21 illustrates Table II, describing the antibodies used in the study of Example 2, as described in detail in Example 2, below.

FIG. 22 illustrates a Table describing PCR primers used in the study of Example 2, as described in detail in Example 2, below.

Like reference symbols in the various drawings indicate like elements.

Figure 1:
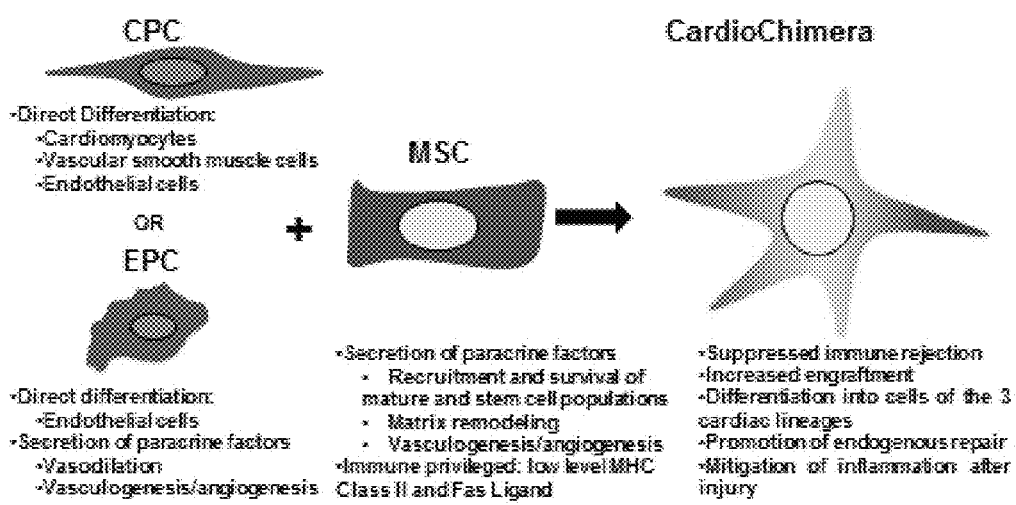
FIG. 1 schematically illustrates an exemplary protocol to merge traits of two unique and distinct stem cell populations, including CPCs or EPCs and MSCs to create cardiochimerias, as described in detail, below.

Reference will now be made in detail to various exemplary embodiments of the invention, examples of which are illustrated in the accompanying drawings. The following detailed description is provided to give the reader a better understanding of certain details of aspects and embodiments as provided herein, and should not be interpreted as a limitation on the scope of the invention.

DETAILED DESCRIPTION

In alternative embodiments, provided are chimeric cells, which in alternative embodiments are so-called "cardiochimeras", and methods for making and using them. In alternative embodiments, chimeric cells as provided herein comprise a cardiac stem cell of cardiac origin or a cardiac progenitor cell (CPC) fused to either a mesenchymal progenitor cell (MPC) or mesenchymal stem cell, an endothelial progenitor cell (EPC) or endothelial stem cell, or a cardiac stem cell or a cardiac progenitor cell. In alternative embodiments, chimeric cells as provided herein comprise an endothelial progenitor cell, which may or may not be of cardiac origin, fused to either a mesenchymal progenitor cell or mesenchymal stem cell, an endothelial progenitor cell or endothelial stem cell, or a cardiac stem cell or a cardiac progenitor cell, or may comprise a cardiac stem cell or cardiac progenitor cell fused with an endothelial progenitor cell or endothelial stem cell. In alternative embodiments, the chimeric cells as provided herein comprise fusion of a human cell to a human cell, a human cell to a non-human cell, or a non-human cell to a non-human cell; for example, in alternative embodiments, provided are human-murine (e.g., rodent, rat, mouse) cell fusion products, or murine to murine cell fusion products.

As demonstrated by the study described in Example 2, below, described herein for the first time is utilization of novel cardiac stem cell hybrids created by cell fusion between CPCs and MSCs, also known as CardioChimeras, to support and enhance combinatorial cell delivery approaches. By inheriting properties of CPCs and MSCs, CardioChimeras exhibit optimal properties such as cardiac commitment and enhanced paracrine secretion. CardioChimeras transplanted after MI improves myocardial structure and reduces infarct size. Importantly, CardioChimeras have increased engraftment in the left ventricle compared to groups treated with CPCs or MSCs individually and/or combined. Mechanistically, CardioChimeras promote an increase in capillary density and preserve cardiomyocyte size in the infarct area 12 weeks after damage. CardioChimeras represent an efficient fused product with beneficial and cardioprotective properties for effective cardiac repair.

In alternative embodiments, methods for making chimeric cells as provided herein further comprise selecting a cell fusion product comprising a viable chimera of the fused cells having a desired set of properties.

In alternative embodiments, methods for making chimeric cells as provided herein comprise use of any known cell fusion technique, for example, using a Sendai virus, such as a Sendai virus Hemagglutinating Virus of Japan Envelope (HVJ-E), a polyethylene glycol, liposomes or lipids, a fusion protein, electrofusion and/or equivalents thereof.

In alternative embodiments, provided are cell lines, chimera (chimeric) cell lines or chromosomally-stable chimera cell lines, derived or made from chimeric cells as provided herein.

In alternative embodiments, provided are methods for inducing cardiogenesis in a mammalian heart comprising administration to an individual in need thereof (for example, a human), chimeric cells as provided herein, or a cell line, a chimera cell line or a chromosomally-stable chimera as provided herein.

In alternative embodiments, provided are methods for treating or ameliorating a heart injury, a congenital or genetic heart defect, or a heart dysfunction, comprising administration to an individual in need thereof (for example, a human), chimeric cells as provided herein, or a cell line, a chimera cell line or a chromosomally-stable chimera as provided herein.

In alternative embodiments, human stem cells from fetal hearts that are in the midst of cardiogenesis or stem cells from adult hearts are used to make exemplary chimeric cells as provided herein. Routine sorting protocols can be used for isolation of cardiac progenitor cells (CPCs), mesenchymal progenitor cells (MSCs) and endothelial progenitor cells (EPCs) from patients of varying age and gender; these can be compared to archetypical fetal stem cells undergoing rapid proliferation.

The inventors found that each stem cell exhibits characteristics that render them desirable to promote a regenerative repair. For example, MSCs are multipotent stem cells that give rise to bone, cartilage and adipose tissue. MSC adoptive transfer to the heart supports endogenous regeneration by secretion of paracrine factors that activate endogenous stem cells, promote angiogenesis, protect cardiomyocytes and reduce scar formation. Furthermore, MSC transplantation suppresses immune rejection, decreasing inflammation after acute MI, due to enhanced secretion of anti-inflammatory factors.

In animal models transplanted CPCs give rise to cardiomyocytes, smooth muscle and endothelial cells, but lack the power of MSCs to activate and recruit endogenous stem cells. EPCs mobilized from bone marrow promote paracrine dependent vasodilation, vasculogenesis and angiogenesis and differentiate into mature endothelial cells.

Combinatorial cell therapies have been suggested in hopes of initiating additive or synergistic effects in myocardial repair such as with the delivery of MSCs and c-kit$^+$ CPCs into an infarcted swine model. However, the retention of adoptively transferred stem cells in general has previously been quite poor regardless of whether it involves single or combinatorial stem cell delivery. More importantly, arbitrary transfer of two or more stem cell populations together does not ensure stem cell interaction and cross talk that are essential for repair of advanced organ damage. In alternative embodiments, these issues are addressed by the ex vivo expansion of chimeric stems cells as provided herein to their transplantation or implantation; thus, in some embodiments, these chimeric cells can retain phenotypic characteristics from each parent cell type, for example enhanced proliferation and survival (characteristic of EPCs) as well as cardiogenic commitment after engraftment into the myocardium (characteristic of CPCs).

In alternative embodiments, the cell fusion as provided herein causes cell reprogramming; thus, genetic factors and phenotypic traits that influence dormant or somatic cell types into undergoing proliferation or commitment can be defined. In alternative embodiments, cell fusions, or the cell chimeras as provided herein, are used in cellular based approaches to treat cardiovascular disease, including repairing the myocardium, and in alternative embodiments can give superior results as compared to using just combinatorial cellular therapy alone.

In alternative embodiments, the cell fusions as provided herein are used to generate novel cell types that can combine traits of two stem cell types. In alternative embodiments, chimeras as provided herein are advantageous over all other stem cell types for cellular repair because the cells as provided herein do not carry the risk of silencing inherent beneficial properties, but rather enhance stem cell capabilities in a synergistic manner. In alternative embodiments, the cell fusions as provided herein create novel cell types resulting from blending between cell types of varying degrees of pluripotency and proliferation potential. Described for the first time herein is the derivation and characterization of chimeras from two distinct stem cell populations from the heart and characterizes their regenerative capabilities.

In alternative embodiments, the cell fusions as provided herein are between CPCs and MSCs or EPCs and MSCs, as presented in FIG. 1, which schematically illustrates an exemplary protocol to merge traits of two unique and distinct stem cell populations. Fusions of EPCs and MSCs are also possible, as well as fusions between selected chimeric cells as described herein with a CPC, an MSC, or an EPC, and fusions between two chimeric cells as described herein. Because traditional approaches using single stem cell populations have confirmed that CPCs, EPCs and MSCs have distinct cellular properties in vitro and in vivo, cellular fusions of stem cells as provided herein produce hybrids that are novel cell types, some of which combine desirable characteristics of the parent cells, e.g., ability to dictate direct and indirect repair of the damaged heart.

In alternative embodiments, chimeric cells as provided herein provide superior regenerative capacity; cells as provided herein can be hybrids that are robust variants that can possess new and/or more extreme traits than their parents, or parental intermediates. The variability seen in cellular hybrids as provided herein can be like the inherent heterogeneity observed in expression of cell surface markers; these lead to distinct transcriptional profiles.

In alternative embodiments, chimeric cells as provided herein are characteristically larger in size, an attribute that can enhance retention of stem cells in vivo compared to their smaller parental counterparts. In alternative embodiments, chimeric cells as provided herein can be screened for traits that are found in the two "parent" stem cell populations to demonstrate properties of enhanced commitment and promotion of endogenous repair when used for adoptive transfer experiments.

In alternative embodiments, chimeric cells as provided herein have therapeutic value that is rationally designed based on known characteristics and functions of the "parent" CPCs, MSCs and EPCs. In alternative embodiments, chimeric cells as provided herein have enhanced commitment into the cardiac lineage, and can provide a protective paracrine milieu in the myocardium. In alternative embodiments, chimeric cells as provided herein are cellular fusions, or cell hybrids, having desired qualities of enhanced proliferation, cell survival, commitment and paracrine gene expression that can support regeneration of damaged organs and advance cell therapy in humans.

In alternative embodiments, chimeric cells as provided herein display improved characteristics of growth, survival, secretion of paracrine factors and cardiac commitment relative to non-fused cell populations. Cellular fusion allows for the derivation and selection of novel man-made cell types that have characteristics of their parent cells. For example, in alternative embodiments, chimeric cells as provided herein comprising human c-kit$^+$ CPCs as at least one of the "parent cells" can be selected to also have immune privileged properties characterized, e.g., by decreased expression of MHC Class II receptors similar to bone marrow derived MSCs.

In alternative embodiments, chimeric cells as provided herein by any cellular fusion process known in the art, e.g., a fusion induced using a Sendai virus or related Paramyxoviridae, e.g., the Sendai virus Hemagglutinating Virus of Japan Envelope (HVJ-E), or murine parainfluenza virus type 1; or, a Semliki Forest virus (SFV); or any equivalent "fusion-generating" virus.

Methods for Administering Chimeric Cells, Cell Lines

In alternative embodiments, chimeric cells as provided herein, or a cell line, a chimera cell line or a chromosomally-stable chimera as provided herein are administered to induce cardiogenesis in a mammalian (e.g., a human) heart, or for treating or ameliorating a heart injury, a congenital or genetic heart defect, or a heart dysfunction. The cells, cells lines and the like can be administered by any means known in the art, for example, by local injection (including e.g., intracoronary, intramyocardial and endocardial routes), infusion or equivalent techniques. In alternative embodiments, chimeric cells as provided herein, or a cell line, a chimera cell line or a chromosomally-stable chimera as provided herein are administered, or delivered in vivo, through coronary arteries, coronary veins, or peripheral veins; or, alternatively, via direct intramyocardial injection using a surgical, transendocardial, or transvenous approach; see e.g., Rosen et al., J Am Coll Cardiol. 2014; 64(9):922-937; Perin et al. Nat Clin Pract Cardiovasc Med. 2006 March; 3 Suppl 1:S110-3. In one embodiment, catheters are used to administer, or deliver, the cells, e.g., ND INFUSION CATHETER™ Translational Research Institute, aka TRI Medical (Frankfurt, Germany).

Techniques for delivering nucleic acids (e.g., gene therapy) to the heart can also be adapted for administration of chimeric cells as provided herein, or a cell line, a chimera cell line or a chromosomally-stable chimera as provided herein. Examples and descriptions of such protocols and techniques that can be used, and adapted, to practice this invention in vivo are e.g., Rasmussen (2011) Circulation, vol 123, pgs 1771-1779; Bridges et al., Annals of Thoracic Surgery, 73: 1939-1946 (2002); Wang, et al., Catheter, Circulation, 2009, pp. S238-S246, vol. 120, suppl. 1. Vulliet, et al., Lancet, Mar. 6, 2004; WO 2005/030292 (Apr. 7, 2005); WO 2005/027995; U.S. Patent application publication 20060258980; U.S. Pat. Nos. 7,722,596; 8,158,119; 8,846,099.

Additionally, materials or delivery adjuvants can be used to enhance cell retention and their longevity once delivered to a heart, e.g., by administration with or formulated with (e.g., mixed with) a gel or a hydrogel, such as a chitosan-based hydrogel, e.g., as described in Kurdi et al. Congest Heart Fail. 2010 May-June; 16(3):132-5, or any biocompatible scaffold, e.g., as described in U.S. Pat. Nos. 8,871,237; 8,753,391; 8,802,081; 8,691,543, or Pagliari et al. Curr Med Chem. 2013; 20(28):3429-47, or biomimetic support, e.g., as described in Karam et al. Biomaterials. 2012 August; 33(23):5683-95.

Kits

Provided are kits comprising compositions as provided herein and methods as provided herein, including chimeric cells as provided herein, or cell lines, chimera (chimeric) cell lines or chromosomally-stable chimera cell lines, derived or made from chimeric cells as provided herein, or any combination thereof. As such, kits, cells, instructions, including descriptions of practice methods as provided herein, and the like are provided.

The invention will be further described with reference to the following examples; however, it is to be understood that the invention is not limited to such examples.

Example 1: Making and Using Exemplary Chimeric Cells

The following example describes making and using chimeric cells as provided herein. In summary: chimeras as provided herein were purified after cell fusion with Hemagglutinating virus of Japan and expanded clonally based on dual expression of fluorescent proteins mCherry and eGFP from CPCs and MSCs respectively. Chimeras as provided herein can be mono-nucleated, can have comparable growth kinetics to parental CPCs and MSCs and can display increased cellular size unrelated to cell cycle arrest and/or senescence. Chimeras as provided herein can have increased expression of cardiomyogenic lineage markers cardiac troponin T (2.5-fold), smooth muscle 22 (9.3-fold), and CD31 (10.7-fold) concomitantly associated with decreased c-kit protein expression (50%) relative to parent CPCs. Lineage commitment of chimeras as provided herein is bolstered by dexamethasone treatment measured by mRNA levels of cardiogenic genes and increases in active mitochondria (2.2-fold) after labeling with MITOTRACKER™ (Life Technologies, Carlsbad, Calif.). Induction of apoptosis is blunted in cardiomyocytes co-cultured with chimeras as provided herein compared to co-culturing with CPCs and MSCs alone, or combination of non-fused parent cells. Chimeras o as provided herein can enhance cardiomyocyte growth similar to parent MSCs owing to an increased propensity to secrete pro-growth factors. Collectively, chimeras as provided herein represent an adaptable cell therapy combining the beneficial properties of CPCs to undergo cardiac specific commitment as well as MSCs that foster an improved microenvironment with protective paracrine secretion. Clinically, chimeras as provided herein merge the application of distinct cell types into a single entity for increased engraftment, mitigation of inflammation and blunting the progression of heart failure by promoting myocardial regeneration.

In an exemplary embodiment, two cell populations to be fused are designed to express differential fluorescent proteins. They are suspended 1:1 with addition of the HVJ-E to induce cellular fusion and then plated in growth media. Fusions have been attempted with stem cells derived from mouse in combinations of CPCs and bone marrow derived MSCs. In alternative embodiments, cellular fusions are with human adult and fetal stem cell combinations. In alternative embodiments, human MSCs are combined with CPC and EPC cell populations. A chimeric combination with fetal and adult stem cells can be performed to evaluate if success of fusion is based on pluripotency and proliferative capabilities.

In alternative embodiments, chimeric cells derived from various fusion combinations are confirmed by immunoblot and flow cytometric analysis for co-expression of GFP and mCH. Chimeric cells can be expanded in vitro with selection media containing both puro and bleo for expansion of cells. Parental stem cells expressing either GFP or mCH alone can be maintained as control cells.

In alternative embodiments, chimeric cells have increased cellular size and/or growth is increased. Measurement of cellular size, growth and proliferation can be measured and compared to parental controls. Immunoblot based analysis can be used to determine expression level of cell cycle proteins and senescent markers of chimeric (and control) cells such as cyclins A, B, D and E as well as cell cycle inhibitors p16, p19, p21 and p27 and p53.

In alternative embodiments, apoptosis and cell death are reduced in exemplary chimeric cells as provided herein, e.g., which can be due to enhanced paracrine secretion of pro-survival and anti-inflammatory cytokines. Treatment of chimeric cells with pro-apoptotic stimuli can be performed with hydrogen peroxide, staurosporine, hypoxia and serum starvation, and they can be compared to parental stem cells. Functional readouts of apoptosis and cell death in chimeric cells can be determined by labeling with Annexin V and a nuclear dye (e.g., a sytox blue, TO-PRO-3™ (Life Technologies, Carlsbad, Calif.), propidium iodide). Protein analysis of molecules, which regulate apoptosis, can be evaluated by probing for anti-apoptotic molecules Bcl-2, Bcl-XL and pro-apoptotic proteins such as phosphorylated BAD and p53. Chimeric cells can be analyzed for cell viability, e.g., by trypan blue exclusion assay, after successive days of plating to determine live versus dead cells during basal conditions and after treatment with apoptotic challenge compared to parental lines.

In alternative embodiments, cardiomyocyte and vascular cell differentiation combined with paracrine secretion will improve the ability of exemplary hybrids and chimeric cells as provided herein to commit to the cardiac lineage and provide for survival and/or proliferation of cardiomyocytes and stem cells after co-culture. Paracrine profiles of chimeric cells as provided herein relative to parental cell lines can be determined with a human cytokine and inflammation PCR arrays. Secondary confirmation of paracrine factors can be determined by qRT-PCR and ELISA to validate secretion of proteins in the supernatant from hybrid cells compared to parental cells. Effects of conditioned media can be evaluated. Effects of direct contact of cells by co-culture of chimeric cells as provided herein on a system of cardiomyocyte survival by incubation with NRCMs can be evaluated. Testing for NRCM viability can be evaluated through morphometric analysis and quantitation after labeling with Annexin V and a nuclear stain followed by flow cytometry. Negative gating against mCH and GFP positive cells by flow cytometry can ensure exclusion of chimeric cells as provided herein for analysis of cardiomyocytes in co-culture conditions. Quantitation of RNA and protein of secreted factors in chimeric cells as provided herein can be compared to parental cells before fusion as a control.

Induction of cardiogenic markers by analysis of mRNA by qRT-PCR can be investigated at basal levels and compared to parental controls. Subsequently, RNA can be isolated from cells after treatment with dexamethasone and co-culture with NRCMs to induce cardiac specific differentiation. Gene expression for a variety of mature cardiac, smooth muscle and endothelial markers can be determined by qRT-PCR. Additionally, cardiogenic proteins can be analyzed by immunoblotting and cell staining followed by immunofluorescence compared to non-fused control cells treated with differentiation stimuli.

In vitro, mouse derived chimeric cells as provided herein exhibit properties that are unique based on initial characterization relative to parental cell lines, such as seen in proliferation patterns and cell morphology. Based on these observations, mouse chimeric cells as provided herein at basal conditions do not appear to have increased cellular death compared to parental cells. Chimeric cells as provided herein can have potential autocrine effects to maintain autonomous survival and paracrine secretion patterns to support mature and stem cell populations in the cardiac setting.

In alternative embodiments, use of EPCs in chimeric cells as provided herein results in cells having a paracrine role in the heart after injection. Cellular fusions between CPCs and EPCs, as EPCs can supplement direct differentiation into the vascular lineages and support endogenous vascular regeneration in combination with de novo cardiomyocyte commitment. Cellular fusion of somatic cells and production of hybrids can lead to the acquisition of a novel chromosome assortment, a normal chromosome number and 2N ploidy status due to chromosomal complementation after mitosis; thus, adult chimeric cells as provided herein can have ploidy status, and flow cytometry can be used to analyze cell cycle profiles beyond 4N. Karyotype analysis can be performed to evaluate the appearance of chromosomes and determine chromosome number.

In alternative embodiments, chimeric cells as provided herein can restore myocardial structure and function after intramyocardial injection better than "cardiospheres" (e.g., self-assembling multicellular clusters from the cellular outgrowth of cardiac explants cultured in nonadhesive substrates) or single or multiple cell suspensions. Thus, in alternative embodiments, stem cell therapy for treatment of heart damage using chimeric cells as provided herein addresses the poor survival of conventionally delivered stem cells, and their inefficient commitment and engraftment.

In alternative embodiments, chimeric cells as provided herein are administered to treat the effects of acute MI, which is characterized by adverse inflammation and secretion of detrimental growth factors that promote fibrotic scar formation. In alternative embodiments, chimeric cells o as provided herein are administered to ameliorate or prevent the irreversible MI myocardial damage, which decreases hemodynamic function and leads to heart failure. In alternative embodiments, chimeric cells as provided herein are administered to augment the myocardium's response to MI, which has modest endogenous regenerative mechanisms to replace lost or damaged cells. In alternative embodiments, chimeric cells as provided herein exploit the combinatorial roles of CPCs, MSCs and EPCs to enhance cardiogenic repair by improvement of commitment and secretion of protective factors.

Methodological Details:

Chimeric cells as provided herein, including CPC-MSC/EPC-MSC chimeras, are injected in the myocardial border zone of an acutely infarcted immunodeficient NOD-SCID mouse heart by ligation of the Left Anterior Descending (LAD) artery prior to delivery and using phosphate buffered saline (PBS) as a vehicle. Negative control groups are maintained by injection of phosphate buffered saline alone (no cellular treatment). Positive controls are maintained by performing sham operations (opening and closing of the chest). PBS and cell treated groups are evaluated for comparable infarct size and impaired ejection fraction (EF) three days post-surgery relative to sham controls using echocardiography. Mice with less than 50% of the left ventricle infarcted within three days of surgery are excluded. Additionally, mice will be sacrificed from each group to determine the efficiency of injection of chimeric cells as provided herein. Control groups for chimeric cells as provided herein can include cellular treatment with CPCs, MSCs, and EPCs that were not pre-formed in clusters but maintained in co-culture or single populations for the same duration as the experimental group, as well as cardiospheres. Injection of control groups for chimeric cells as provided herein can include combinatorial therapy of non-fused CPCs and MSCs or EPCs and MSCs.

After intramyocardial injection of chimeric cells as provided herein, detection and quantitation of stem cell treatments are determined by immunohistochemistry by labeling the chimeric cells to express a detectable moiety, e.g., a single fluorescent protein or co-expression of both GFP and mCherry in a chimera, to determine engraftment relative to control groups. FIG. 3 schematically illustrates lentiviral constructs used to label and identify stem cells in vitro and in vivo. Lentiviral constructs were created with use of the human phosphoglycerate kinase promoter to express enhanced green fluorescent protein (eGFP), mCherry (mCH) or mKusabira orange (mKo) proteins followed by the murine PGK promoter to express puromycin (puro) or bleocin (bleo) selectable markers. All stem cells are transduced with lentiviruses prior to experimental protocols, and express fluorescent markers within 48 hours. If expression of fluorophore is less than 80% after flow cytometric analysis cells will be purified for fluorescent tags by treatment with either puro or bleo. These fluorescent markers were chosen due to non-overlapping spectral emissions for flow activated cell sorting methods. Specific antibodies to detect eGFP, mCherry and mKO proteins in biochemical assays such as immunoblotting, immunocytochemistry and immunohistochemistry can be used for identification.

Morphological analysis of the transplanted stem cells within the myocardium can be analyzed to e.g., determine morphology of the chimeric cells, e.g., if the cells, have formed spherical formations or dissociated into single cell types.

Cardiac Structure and Function is Enhanced by Injection of Exemplary Chimeric Cells.

Cell treatment to affect cardiac function can be measured each week after infarction and treatment up to four weeks to validate the short-term effects of the in vivo transplantation. Administration of chimeric cells as provided herein can result in increases in EF and fractional shortening, possibly within weeks.

Mice are subjected to in vivo hemodynamics by inserting a pressure-volume catheter through the carotid artery to enter the left ventricle. Measurements obtained can determine end diastolic and end systolic pressure as well as developed pressure (maximum and minimum mmHg/seconds) to evaluate cardiac functional parameters using a VEVO 2200™ echocardiographic machine. Remaining mice in each group will be maintained to evaluate the long-term effect of in vivo administration of cells as provided herein, such as every two weeks following hemodynamics until twelve weeks after injection or longer. Before completion of the experiment, all mice are subjected to in vivo hemodynamics, and sacrificed by retroperfusion to fix the heart in diastole with formalin before embedded in paraffin to create sections for immunohistochemistry. Tibia length and heart, body and lung weights are measured to determine relative physiological health such as congestive heart failure (Lung weight/body weight) and cardiac hypertrophy (heart weight/body weight or tibia length). For analysis of longitudinal assessment, animal heart function is statistically evaluated using two-way ANOVA to determine differences in cardiac function over time.

Cardiac improvement is correlated with inhibition of adverse remodeling after infarction such as reduced scar formation and prevention of dilation. Similar to cardiac functional analysis, dilation of the left ventricle can be determined by echocardiography, which will accurately quantify ventricular volume and mass. Tissue Doppler imaging can be used to test the applicability of our cellular treatments to affect myocardial tissue strain and wall stress, by analyzing the motion of diverse structural components of the heart. Anterior wall thickness can be measured to determine the rescue of infarcted myocardium by injection of cells as provided herein in the anterior wall of the myocardium. Formation of fibrotic scarring and left ventricular infarct size can be analyzed by Masson's Trichome staining and immunohistochemistry to quantify the percentage of surviving myocardium relative to scar formation after cellular treatment using antibodies against tropomyosin (cardiomyocytes) and pro-collagen and collagen I and III (scar tissue). Fibrosis and infarct size measurements at an early and late time point can be analyzed with at least five mice per group and one-way ANOVA statistical analysis to determine significance between experimental groups.

Direct Commitment of Exemplary Chimeric Cells is Improved as Evidenced by Increased Formation of Myocytes, Endothelial and Vascular Smooth Muscle Cells and Structures.

Chimeric cells as provided herein can be analyzed for morphology and expression of cardiac progenitor transcription factors GATA-4, Mef-2 and Nkx2.5 and c-kit, MSC markers CD105 and CD90 and EPC expressing CD133 to determine if cells retain stem cell characteristics after different time points after injection. To confirm direct commitment, co-labeling with proteins that define sarcomeres and cardiomyocyte structure can be performed with labeling of α-sarcomeric actin and/or tropomyosin with fluorescent transgenes. Identification of stem cell derived supporting cells of the cardiogenic lineage, GFP, mKO and mCH cells can be co-stained with markers of mature vascular smooth muscle and vascular endothelium identified with antibodies against α-SMA, GATA-6, smooth muscle 22 and vWF. Fluorescently tagged cells that are also co-labeled for mature cardiac markers can be analyzed for telomere length to define young cardiac cells relative to the surviving mature myocytes using a telomere fluorescence in situ hybridization (FISH) protocol on immunohistochemical sections.

Endogenous Stem Cell Population Proliferation, Survival and Recruitment are Enhanced by Injection of Exemplary Chimeric Cells.

Injection or administration of chimeric cells as provided herein results in mobilization of endogenous stem cells, including delivery of growth factors such as leukocyte inhibitory factor and stromal derived growth factor to promote beneficial effects on cardiac function. Recruitment of stem cells in the infarcted myocardium following administration of chimeric cells as provided herein can be identified by immunohistochemistry in order to quantitate the number of c-kit$^+$ cells that are not expressing fluorescent markers within the infarcted region. To distinguish between cardiac resident c-kit$^+$ cells or cells mobilized from the bone marrow, numbers of c-kit$^+$ cells that co-express hematopoietic markers such as CD45 or CD34 (myeloid progenitor marker) can be determined. Assessment of proliferation and expansion of c-kit$^+$ stem cells can be evaluated for proliferation markers such as Ki67, proliferating cell nuclear antigen (PCNA) and increased cells undergoing mitosis by detection of phosphorylated histone H3 in both the fluorescent negative and fluorescent positive populations within the heart. These studies can be performed at the early time point, for example, at one to four weeks after MI, to determine if chimeric cells as provided herein supply a paracrine effect relative to delivery of single or combinatorial stem cell populations.

Injection or administration of chimeric cells as provided herein results in rescuing or salvaging existing cardiomyocytes; this can be evaluated by using a terminal deoxynucleotidyl transferase dUTP nick end labeling (TUNEL) assay in tropomyosin/a-sarcomeric actin positive cardiomyocytes at an early time point after infarction and intramyocardial injection, for example, at 3 to 7 days after MI. Delivery of chimeric cells as provided herein can promote endogenous regeneration in addition to improving cardiac repair via enhanced lineage commitment.

Figure 2:
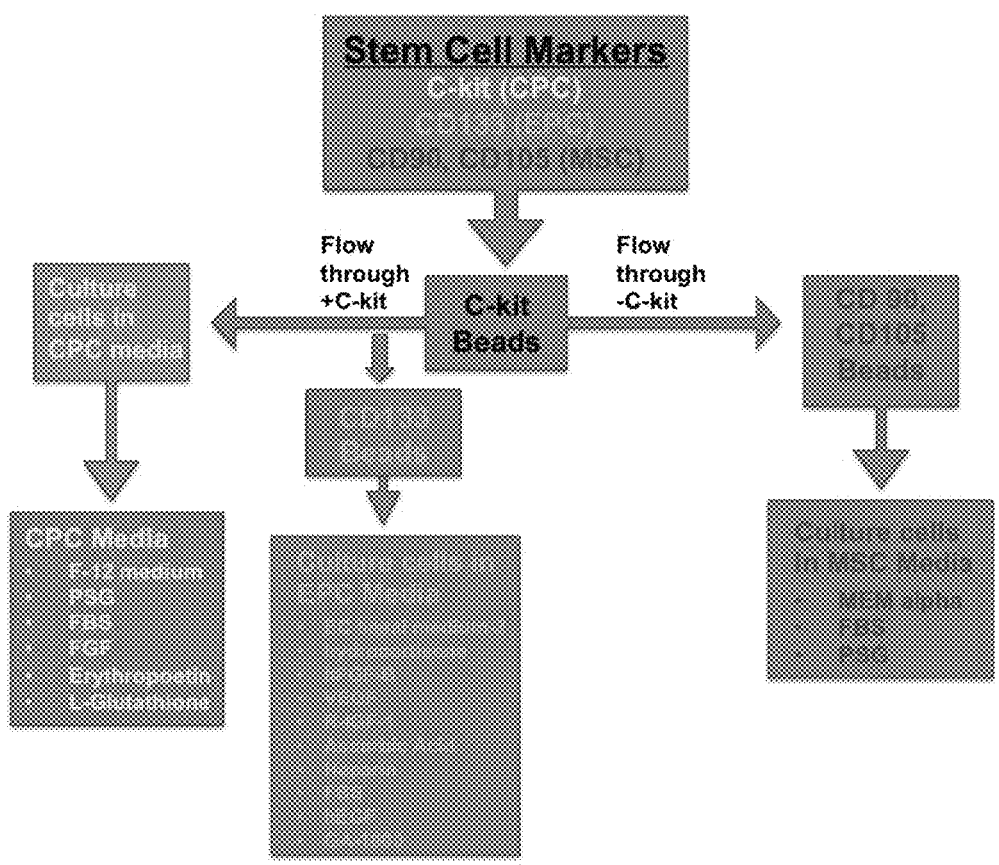
FIG. 2 schematically illustrates an exemplary protocol for magnetic bead separation of stem cells from human myocardial samples, as described in detail in Example 1, below.

FIG. 2 schematically illustrates an exemplary magnetic bead separation of stem cells from human myocardial samples. Stem cells were isolated from both whole fetal hearts and adult tissue samples from patients undergoing surgery for left ventricular assist device, or LVAD (a mechanical pump) implantation. Tissue is digested in collagenase and incubated with c-kit labeled beads and subjected to magnetic activated cell sorting. The positive and negative c-kit fractions are collected in order to establish CPC and EPCs (c-kit$^+$) separate from MSCs (c-kit$^-$) as schematically illustrated in FIG. 2. Cells types are validated by flow cytometric analysis to express markers that define them as CPCs, EPCs and MSCs after sorting and expansion. C-kit$^+$ were plated immediately as CPCs. The remaining c-kit$^+$ fraction was sorted for EPCs by expression of CD133. MSCs were derived by CD90 and CD150 expression of the c-kit$^-$ fraction. Each cell type is then plated and expanded in their respective media.

FIG. 4 illustrates images of the surface characterization of cardiac derived stem cells, and graphically illustrates data therefrom: A(1). and A(2). CPCs express c-kit, B(1). and B(2). MSCs express CD105 and CD90, and C(1). and C(2) EPCs express CD133, CD31, and c-kit confirmed by immunocytochemistry and flow cytometric analysis.

FIG. 5 illustrates images of the phenotypic characteristics of cardiac derived stem cells, and graphically illustrates data therefrom: representative images of A. CPCs, B. MSCs, and C. EPCs using light microscopy. Proliferation rates of stem cells (P) 6-8 quantitated by D. cell counting and E. CyQuant assay represented as fold change compared to day of plating.

Based on preliminary morphological data of mouse chimeric cells as provided herein, the sizes of cells and structures are increased, which can substantially improve the retention of cellular treatments as provided herein. In alternative embodiments, engraftment of chimeric cells as provided herein is integral to sustaining regeneration of the myocardium.

Figure 6C:
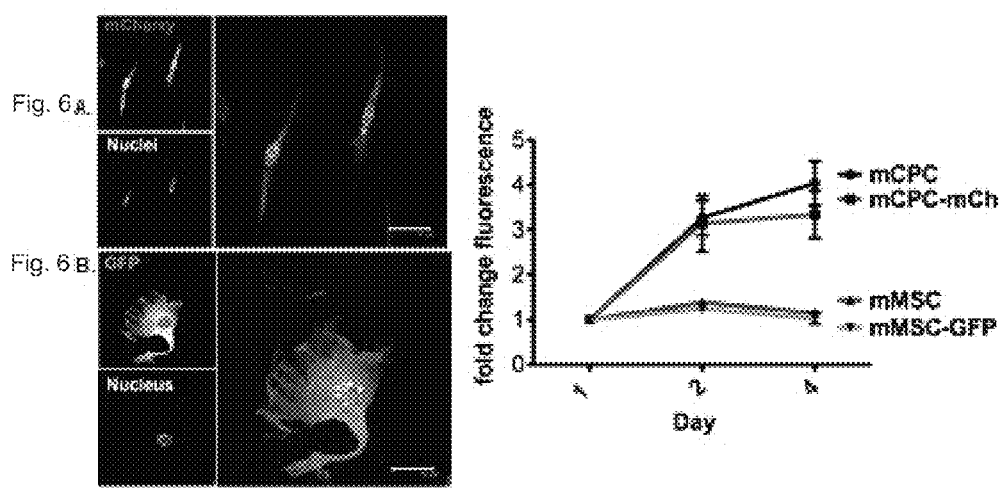

Characterization of Exemplary Mouse Chimeric Cells:

The high proliferation rate of a stem cell population is essential for the reprogramming ability of somatic cells. In our initial studies we compared two populations of stem cells from mouse, c-kit$^+$ CPCs and bone marrow derived MSCs. Mouse CPCs and MSCs were infected with mCH and GFP lentiviruses respectively pre-fusion and confirmed by immunofluorescence, see FIG. 6A and FIG. 6B. FIG. 6 illustrates images of the characterization of c-kit$^+$ CPCs and MSCs, and graphically illustrates the results therefrom: A. CPCs expressing mCherry and B. MSCs expressing GFP as determined by immunofluorescence. TO-PRO-3 stain was used to label nuclei. C. Proliferation rates of non-infected and transduced CPCs and MSCs as measured by cyquant assay and represented as a fold change fluorescence compared to day of plating. Mouse CPCs had increased proliferation rates compared to MSCs measured by cyquant assay, but proliferation was unaffected after transduction with mCH or GFP viruses, as illustrated in FIG. 6C.

Using HVJ-E to induce cell fusion, mCH and GFP positive cells were single cell sorted using FACS and mono-nucleated hybrids were expanded to ensure cultures of homogenous chimeric cells as provided herein, as evidenced by the clone G.8, as illustrated in FIG. 6(B), which expresses mCH and GFP, as illustrated in FIG. 7A. CPC-MSC chimeric cells as provided herein showed proliferation rates that were variable relative to non-fused CPCs and MSCs parental cells (FIG. 8). The E.2 (A) clone was the fastest growing hybrid; the F.2 (B) had a proliferative capacity similar to MSCs, as the three cell hybrids (E.12 (B), G.8 (B) and G.5 (B) showed similar proliferation rates as CPCs.

Figure 7:
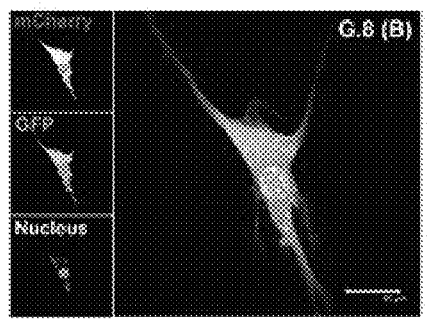
FIG. 7A and FIG. 7B illustrate images of the characterization of CPC-MSC hybrids, and graphically illustrates data therefrom.
Figure 7:
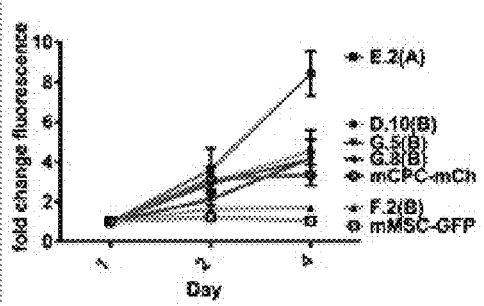
Figure 8:
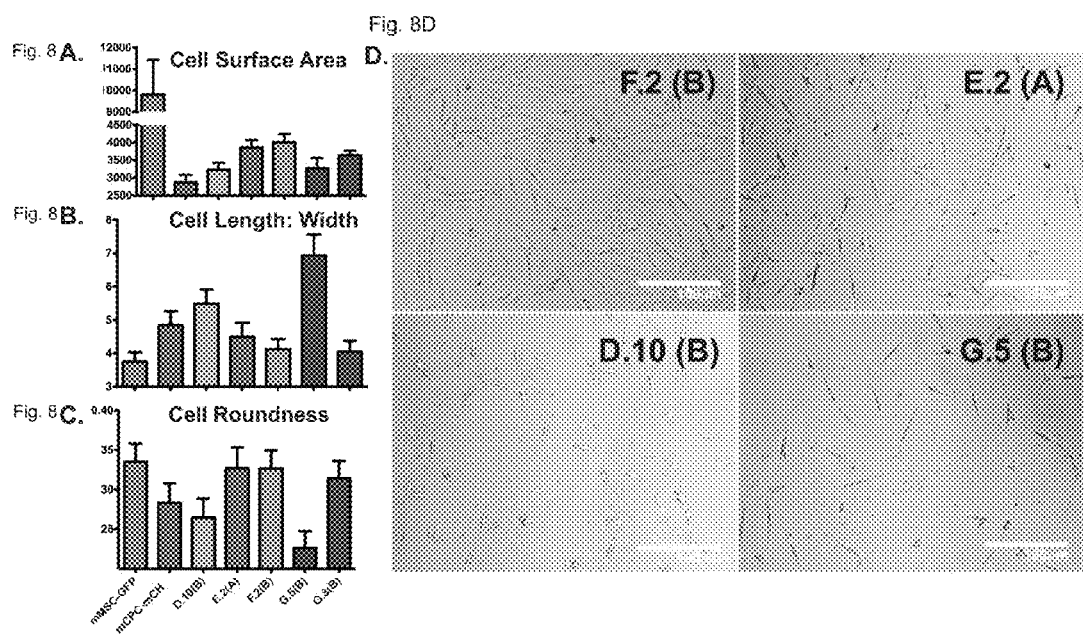
FIG. 8A, FIG. 8B, FIG. 8C, FIG. 8D illustrate images of a morphometric analysis of CPC-MSC hybrids, and graphically illustrates data therefrom.

FIG. 7 illustrates images of the characterization of CPC-MSC hybrids, and graphically illustrates data therefrom: A. Representative image of a stem cell hybrid derived after fusion of mouse c-kit$^+$ CPCs with MSCs. The novel cell type is a mono-nucleated cell after labeling with TO-PRO-3, a nuclear stain. B. Proliferation rates of CPC-MSC hybrids were quantitated by CyQuant assay and represented as a fold change fluorescence compared to day of plating relative to parental cells expressing mCh or GFP alone.

The morphological assessments of CPC-MSC chimerics as provided herein were assessed after witnessing distinct cellular phenotypes. The cell surface area of MSCs is significantly larger than CPCs and chimeric cells as provided herein after cell size measurements and immunofluorescence, as illustrated in FIG. 6A and FIG. 8A. Chimeric cells as provided herein show a trend toward increased cell surface area relative to CPCs such as seen in clones E.2, (A) and F.2 (B), as illustrated in FIG. 8A. Interestingly these same two clones appeared to have similar morphological phenotypes such as a decreased length to width ratio, as illustrated in FIG. 8B, which correlates with increased roundness, as illustrated in FIG. 8C, of the cells. Representative images of chimeric cells as provided herein used for measurements are shown in FIG. 8D). The data presented with mice cells presents proof-of-principle for the creation of chimeric cells as provided herein. FIG. 8 illustrates images of a morphometric analysis of CPC-MSC hybrids, and graphically illustrates data therefrom: A. Relative cell surface area B. Cell length to width ratio and C. Cell roundness was measured in hybrids compared to parental cell lines. D. Representative images of four stem cell hybrids using light microscopy. Images were processed for cell measurements quantitated in A, B and C panels.

In summary, these data support the generation of chimeric cells as provided herein by cellular fusion to treat a pathologically damaged heart. Administration of chimeric cells as provided herein can enhance stem cells from the human heart to favor growth, proliferation, survival and paracrine secretion to improve autologous stem cell therapy.

Example 2: Making and Using Exemplary Chimeric Cells

The following example describes exemplary methods as provided herein using exemplary cells provided herein, and demonstrating the efficacy of exemplary compositions and methods provided herein, including that dual cell transplantation of cardiac progenitor cells (CPCs) and mesenchymal stem cells (MSCs) after infarction improves myocardial repair and performance in animals relative to delivery of either cell population by use of large animal models. Data provided here demonstrates that exemplary CardioChimeras (CCs) formed by fusion between CPCs and MSCs have enhanced reparative potential relative to individual stem cells or combined cell delivery as demonstrated using an art-accepted model of myocardial infarction (a mouse model).

Two distinct and clonally derived CCs, CC1 and CC2 were utilized for this study. CCs improved left ventricular anterior wall thickness (AWT) at 4 weeks post injury, but only CC1 treatment preserved AWT at 18 weeks. Ejection fraction was enhanced at 6 weeks in CCs, and functional improvements were maintained in CCs and CPC+MSC groups at 18 weeks. Infarct size was decreased in CCs, whereas CPC+MSC and CPC parent groups remained unchanged at 12 weeks. CCs exhibited increased persistence, engraftment, and expression of early commitment markers within the border zone relative to combinatorial and individual cell population-injected groups. CCs increased capillary density and preserved cardiomyocyte size in the infarcted regions suggesting CCs role in protective paracrine secretion.

Provided herein are CCs that merge the application of distinct cells into a single entity for cellular therapeutic intervention in the progression of heart failure. CCs as provided herein, and methods provided herein, provide a novel cell-based therapy that improves upon combinatorial cell approaches to support myocardial regeneration.

This Example describes the creation and characterization of exemplary CPC and MSC hybrids, referred to as CardioChimeras (CCs), generated by ex vivo viral cell fusion. CCs exhibit enhanced molecular and phenotypic traits relative to individual stem cells and these distinct hybrids were evaluated for in vivo therapeutic effects after myocardial damage in a mouse model. Recovery of anterior wall thickness (AWT) and ejection fraction (EF) were markedly improved, concomitant with increased engraftment and expression of early cardiomyogenic lineage markers in CC treated hearts. Thus, provided are CardioChimeras, and methods of using them, demonstrated to be an effective novel therapeutic that complements the paracrine effects of MSCs to orchestrate endogenous repair with direct cell contributions from CPCs in promotion of de novo cellular regeneration.

Methods

Cell Fusion and Creation of CardioChimeras

Cell fusion was conducted using the GenomONE™-CF EX Sendai virus (Hemagglutinating Virus of Japan or HVJ) Envelope Cell Fusion Kit (Cosmo Bio. USA). According to the manufacturer's protocol, we subjected MSCs and CPCs to the plating method of cell fusion. Here, 100,000 MSCs expressing GFP in a 100 mm dish were incubated in CPC media for 24 hours. Next day, 100,000 CPCs expressing mcherry were suspended in 20 µL of cell fusion buffer and 10 µL of Sendai virus and placed on ice for 5 minutes for absorption of the virus on the cell membrane. Media from the MSC plate was removed and washed once with cell fusion buffer, and CPCs plus Sendai virus was added. The plate was then centrifuged (10 minutes, 1200 rpm at 4° C.) to force cell-to-cell contact. Cells were placed at 37° C. for a total of 15 minutes to induce cell fusion. Non-fused CPCs were removed and media was added back to the plate. The next day, media was changed, and within 48 hours cells were trypsinized and subjected to FACS to place one-cell per well of a 96-micro plate to allow for clonal expansion of double fluorescence cell populations.

Study Design

In vitro studies were designed to predict the reparative potential of CPCs, MSCs, CPC+ MSC and CardioChimeras (CCs) in a mouse model of injury. Cell-to-cell fusion yielded 18 CC clones from a total of 192 wells. For ease in naming clones, we identified CCs based on well number followed by A ($1^{st}$ 96-well plate) or B ($2^{nd}$ 96-well plate). Selected CCs were analyzed for proliferation, survival and paracrine mediated effects on cardiomyocytes and/or expression of cardiomyogenic commitment markers (Figure III of Example 2, or FIG. 17). The 18 CCs exhibited variable proliferative capabilities relative to individual CPCs and MSCs and were classified as slow, slow-medium, medium-fast and fast growing clones based on a 1-2 fold, 2-4 fold, 4-6 fold or >6 fold change in fluorescence relative to day of plating respectively (Figure IA of Example 2, or FIG. 15A). A number of slow-growing CCs were excluded due to a low expansion rate (Figure IA and Table I, or FIG. 20). We further characterized two-three clones per proliferative status for analysis of cell death after oxidative stress and morphological features such as cell size. With the addition of 4004 hydrogen peroxide, 4 CCs were excluded D.6 (A), B.10 (A), D.10 (A), E.10 (A) due to poor cell survival (Figure IB and Table I, or FIG. 20). Although cell size was not a defining reason for exclusion, cell morphological assessments correlated CC phenotype to individual parent cells. CC1 (F.7 (A)) and A.3 (A) exhibited a similar cell surface area to MSCs, whereas the majority of CCs including CC2 (E.2(A)) had a similar surface area to CPCs (Figure IC). Furthermore, co-culturing CCs with NRCMs mediated the identification of clones that could facilitate survival and growth of cardiomyocytes as compared to parent MSCs. Neonatal rat cardiomyocytes (NRCMs) were maintained in low serum (0.5% Fetal Bovine Serum) for 24 hours followed by the addition of CCs, CPCs, MSCs or CPCs and MSCs combined for an additional 24 hours and cardiomyocyte size and cell death was measured (Figure I, D and E). CCs were considered based on the ability to promote cardiomyocyte growth and prevent cardiomyocyte cell death following co-culture (Table I, or FIG. 20). Of the four candidates for adoptive transfer studies, F.9(B) and G.7(B) were eliminated due to a lower proliferative status (Table I, or FIG. 20). These initial analyses facilitated the identification of CCs that are suitable for cardiac therapy during acute damage by identification of clones with optimal proliferation and survival properties in addition to displaying the potential to secrete protective factors to preserve cardiomyocyte health.

For the adoptive transfer analysis, we required approximately 16 animals per cell group to allow for analysis of at 3-5 mice per time point (4, 12 and 18 WPI) without impacting on statistical significance obtained during longitudinal assessment by echocardiography. This number was chosen based on an average of 65-75% survival rate immediately after injury. Mice with a measured. EF between 35-50% one-week post infarction were included in the experiment. EF>50% or <35% were excluded from the experiment. Throughout the time course, mice were not subjected to echocardiography if mice were perceived to be in distress. The study was concluded after determining statistical significance in wall thickness recovery and EF at 18 WPI. The study was not randomized, but was blinded to the operator during echocardiographic acquisition and analysis.

CPC and MSC Isolation

CPCs were isolated and maintained as previously described[1]. CPCs were used during passages 10-20. Mesenchymal stem cells were isolated from 12 week old female FVB mice by flushing the femur and tibiae with 5% Fetal Bovine Serum in PBS through a 40-μm filter and centrifuged (10 minutes, 600 g, 4° C.). Cells were resuspended in media consisting of a modified minimum essential media and 15% FBS. Cells were plated in 150 mm dish and media was changed every two days to remove non-adherent cells. Adherent cells created colonies in approximately two weeks. MSCs were passaged using 0.25% Trypsin and used during passages 2-4 for experiments.

Lentiviral Constructs and Stem Cell Transduction

A third generation enhanced green fluorescent protein (eGFP) lentivirus with a phosphoglycerate kinase (PGK) and puromycin (puro) selection marker was purchased from Addgene. pLenti PGK GFP Puro was used as a backbone to sub clone mcherry in the place of eGFP and bleomycin (bleo) to replace the puro gene in order to create pLenti PGK mcherry Bleo. MSCs at passage 1 were lentivirally transduced with pLenti PGK GFP Puro at a multiplicity of infection (MOI) of 50 and maintained in puromycin supplemented MSC media for one week starting at 48 hours post-infection. CPCs at passage 10 were lentivirally transduced with pLenti PGK mcherry Bleo at a MOT of 10 and subjected to fluorescent activated cell sorting (FACS) to purify mcherry positive CPCs. Fluorescent protein expression in MSCs (MSC-GFP) and CPCs (CPC-mcherry) was confirmed by fluorescent light microscopy and flow cytometric analysis.

Light Microscopy and Measurement of Cell Morphology

Images of stem cells were obtained on a Leica DMIL microscope and cell outlines were traced using ImageJ software. Relative surface area was determined as previously described[2].

Centromere Labeling (Fluorescence In Situ Hybridization)

Cells were fixed on glass two chamber slides in 3:1 ethanol:acetic acid for 30 minutes and then passed through graded alcohol series 70, 90, 100% (2 minutes each step). Slides were baked at 65° C. for 15 minutes and then transferred to acetone for 10 minutes. Slides were then incubated for 1 h at 37° C. in 2×SSC (NACl/NA Citrate)+ RNase (100 μg/ml). Cell were treated with pepsin, 10 mM HCl mixed with 0.5 μl of stock pepsin solution (1 mg/ml) at room temperature for 2-3 minutes and then dehydrated through ethanol series. Denaturing cellular DNA was done by immersing slides in 70% formamide in 2×SSC at 70° C. for 2 minutes and then placed in ice cold 70% ethanol for 2 minutes followed by passing through an ethanol series. Prior to hybridization the centromere probe, CENPB-Cy3 (PNA Bio; ATTCGTTGGAAACGGGA) (SEQ ID NO:1). was warmed to 37° C. for 5 minutes. The probe was denatured for 10 minutes at 85° C. then immediately chilled on ice before applying probe to the slides. The hybridization protocol required 16 hours at 37° C. Post hybridization washes for 5 minutes at 37° C. in 2×SSC were followed by two washes in 50% formamide/2×SSC 37° C., for 5 min each time and final wash in 2×SSC, twice for 5 min each time. DAPI (Sigma-Aldrich) was added to the final wash. Cell nuclei were visualized using a Leica TCS SP8 confocal microscope and the Z-stacking feature. Measurements of nuclear size and centromere intensity were determined after outlining the nucleus and getting the area (μm2) and mean gray values (fluorescent intensity/μm2) after creating a projection of Z-Stack scans.

Proliferation Assay and Cell Doubling Time

Cell proliferation was determined using the CyQuant Direct Cell Proliferation Assay (Life Technologies) according the manufacturer's instruction and as previously described[2]. Population doubling times were calculated using the readings from CyQuant Direct Proliferation Assay and use of a population doubling time calculator (http://www-.doubling-time.com/compute.php).

Cell Death Assay

Stem cells were plated in a 6-well dish (80,000 cells per well) and incubated in starvation media (growth factor and FBS depleted media) with 1% PSG for 18 hours. The cells were then treated with either 40 μM or 80 μM hydrogen peroxide for 4 hours. Cells were resuspended with Sytox Blue (Life Technologies) to label necrotic cells. Data was acquired on a FACS Aria (BD Biosciences) and analyzed with FACS Diva software (BD Biosciences). Cell death was quantitated by measurement of Sytox Blue positive cells and represented as a fold change relative to cells in starvation media alone.

In co-culture conditions of stem cells with NRCMs, whole populations were analyzed and stained with Annexin V (BD Biosciences) and Sytox Blue and only the negative (non-fluorescent NRCM) population was analyzed for cell death. Cell death of NRCMs was represented as a fold change relative to cells in growth media (10% M199). NRCMs in 0.5% M199 and 0.5% plus add back of 10% M199 at the time of stem cell addition were maintained as positive and negative controls for cell death.

Neonatal Rat Cardiomyocyte (NRCM) Co-Culture with Stem Cells

NRCMs were isolated and plated as previously described[3]. After enzymatic digestion, cells were plated in M199 media (Life Technologies) with 15% FBS (Omega Scientific Inc.) at a density of 260,000 cells per well of a 6-well culture dish pretreated with 1% gelatin (Sigma-Aldrich). Within 18 hours, myocyte cultures were washed with PBS and incubated with M199 with 10% fetal bovine serum for 24 hours. The next morning, the cells were subjected to serum starvation (0.5% FBS in M199) for 24 hours. After low serum conditions, stem cells were added to the plate at a ratio of 1:10 (CPCs, MSCs, CPC+MSC combined, CC1 and CC2) and allowed to incubate with NRCMs for an additional 24 hours in low serum conditions. Controls for NRCMs included leaving cells in 0.5% alone, adding back 10% M199 or maintaining NRCMS in 10% M199 for the duration of the experiment. NRCM size was measured after staining cardiomyocytes with sarcomeric actinin (1:100, Sigma-Aldrich) and nuclei with TO-PRO-3 iodide and as previously described[4]. Separation of NRCM and stem cells was accomplished with fluorescent activated cell sorting (FACS) of negative cells (NRCMs) versus GFP$^+$, mcherry$^+$ or GFP$^+$/mcherry$^+$ stem cells. After sorting, cells were centrifuged and suspended in RNAse buffer for isolation and quantitation of mRNA from NRCMs or stem cells.

Immunocytochemistry

Stem cells were placed at a density of 15,000 per well of a two-chamber permanox slide and stained according to previous studies[5]. Before scanning, cells were washed in PBS containing TO-PRO-3 iodide (Life Technologies) to stain for nuclei. Slides were visualized using a Leica TCS SP2 confocal microscope. Primary and secondary antibodies used are listed in Table S2.

Flow Cytometric Analysis

Cells in suspension were counted (200,000 cells per sample) and stained with primary and secondary antibodies as indicated in Table II, or FIG. 21. Samples were analyzed using a FACS Canto (BD Biosciences).

mRNA Isolation, cDNA Synthesis and Quantitative RT-PCR

RNA was enriched using the Quick RNA Mini Prep kit from ZymoResearch according to the manufacturers instructions. Reverse transcriptase was performed using protocol for the iScript cDNA Synthesis Kit (BIORAD). qRT-PCR was read after incubation of cDNA, primers (100 nM) and IQ SYBR Green Supermix (BIORAD). Data was analyzed using the ΔΔC(t). Primer sequences are illustrated in FIG. 22.

Enzyme-Linked Immuno Assay (ELISA)

The ELISA assay was performed in NRCMs alone (0.5%, 0.5%+10% rescue, and 10% M199 treated cells), NRCMs incubated with stem cell groups and stem cells alone in normal growth media. Briefly, after 24 hour incubation with serum or stem cells, the 96-well microplate was centrifuged for 5 minutes at 1200 rpm and 100ℓ of media supernatant was removed and used for IL-6 Mouse ELISA Kit (Life Technologies) performed according the company's instructions.

Myocardial Infarction and Intramyocardial Cell Injections

Myocardial infarctions were carried out in eleven-week old female FVB mice under 2-3% isoflurane anesthesia and by tying off the left anterior descending artery (LAD) using a modified protocol[20]. After ligation, injections with either PBS (54 per injection, 5 injections total per mouse), parents (CPCs or MSCs), parents combined (CPC+MSC) or CCs CC1 (20,000 cells per 5 μL injection, 5 injections making a total of 100,000 cells injected per mouse) were introduced to the pre-ischemic border. Placing the heart out of the chest and placing it back in the chest without ligation of the LAD was considered a sham surgery. The review board of the Institutional Animal Care and Use Committee at San Diego State University approved all animal protocols and studies.

Retroperfusion

Mice were sacrificed under chloral hydrate sedation before removing hearts from mice and as previously described[1]. After retroperfusion, hearts were processed for paraffin embedding.

Immunohistochemistry

Heart sections were deparaffinized, and incubated with primary and secondary antibodies as previously described[5]. Subsequent tyramide amplification was performed as necessary. Slides were incubated in DAPI (Sigma-Aldrich) for 10 minutes to stain for nuclei. Primary and secondary antibodies used are listed in Table II, or FIG. 21.

Echocardiography and Hemodynamics

Echocardiography was used to evaluate cardiac function after MI and injections using the Vevo 2100 (Visual Sonics) and as previously described[5]. Closed-chest hemodynamic assessment was performed after insertion of a microtip pressure transducer (FT111B, Scisense) and as previously described[5]. Cardiac function assessed by echocardiography 2 days post-infarction was not statistically different between infarcted/injected groups. The review board of the Institutional Animal Care and Use Committee at San Diego State University approved all animal protocols and studies.

Quantitation of c-Kit Cells, Infarct Size and Cellular Engraftment

Paraffin sections were probed with primary antibodies for proteins cardiac troponin T, c-kit, GFP and mcherry and visualized on a Leica TCS SP8 Confocal Microscope. Nuclei were visualized after DAPI staining. For infarct size, cTNT was probed to visualize live myocardium and DAPI to determine nuclei distribution and area of infarction. Area of live versus dead myocardium was measured using the drawing tool in the Leica Software and normalized to the total area of the left ventricular free wall and converted to percentage. In this area, c-kit$^+$ cells were counted. For engraftment, area of mcherry$^+$ (CPCs, CPCs in CPC+MSC group, CC1 and CC2) or GFP$^+$ (MSCs alone and MSCs in CPC+MSC group) was measured and normalized to total area. 4 and 12 week sections had an N=3-4 hearts per group.

Isolectin Staining and Measurement of Capillary Dimensions

Paraffin sections were probed with Isolectin B4-488 (Life Technologies) in combination with cTNT and DAPI. Scans consisted of border zone and infarct regions for each heart analyzed. The analysis software on the Leica SP8, quantitated the number of positive cells in each field of view. The area of the field of view was measured and used to normalize capillary numbers per mm$^2$. An N=3-4 hearts per group was measured.

Measurement of Cardiomyocyte Hypertrophy

Paraffin sections were stained for cTNT to visualize live myocardium, wheat germ agglutinin-555 (Life Technologies) to outline cardiomyocyte membrane and DAPI to visualize nuclei and area of infarction. Myocytes were measured in the border zone of the infarct or in this infarct. Cross-sectional views of cardiomyocytes were considered and measured using the drawing tool to determine area using the SP8 TCS Leica Software. An N=3-4 hearts per group was measured.

Masson's Trichrome

Trichrome (Masson) kit was used to stain for collagen deposition in infarcted hearts according to manufacturer's protocol and based on previous reports[1]. Staining was visualized using a Leica DMIL microscope.

Statistical Analyses

All data are expressed as mean+/−SEM. Statistical analyses was done using paired or unpaired Student's t-test, one-way ANOVA or two-way ANOVA with a Dunnett post-test to compare groups to a control group using Graph Pad Prism v5.0. A value of p<0.05 was considered statistically significant.

Results

Phenotypic Characterization of CardioChimeras

CardioChimeras (CCs) were created after fusion of fluorescently labeled CPCs (mcherry) and MSCs (eGFP) with an inactivated RNA Sendai virus (FIG. 1A). After fusion, dual fluorescent hybrids were purified by fluorescent activated cell sorting and allowed to undergo clonal expansion (FIG. 1A and Figure IIA of Example 2, or FIG. 16A). 18 mononucleated hybrids were successfully expanded one-month after initial sorting. Additional information concerning the analysis and selection criteria of the two CCs from the 18 clones is described in Figure I or FIG. 15, and Table I, or FIG. 20. CC1 and CC2 were chosen from the 18 clones due to enhanced proliferation relative to the majority of clones, optimal cell survival, and the ability to provide pro-growth and survival factors when co-incubated with cardiomyocytes (Figure I or FIG. 15, A-E and Table I, or FIG. 20). CC2 exhibits a proliferative rate similar to CPCs while CC1 shows modest proliferation, and all cells had increased proliferation over MSCs based on a fluorescent dependent cell proliferation assay and cell doubling time (FIGS. 1, B and C). CCs are not increasingly susceptible to cell death compared to parent cells (FIG. 1D) and do not exhibit elevated expression of cell cycle arrest or senescence markers based on mRNA for p16 or p53 (FIGS. 1, E and F). CC1 has increased cell size and is morphologically similar to MSCs (FIGS. 1, G, I and J). CC2 displays a slight increase in cell size but is not significantly different from CPCs (FIGS. 1, G, H, and K). Mononucleated CC1 and CC2 exhibit increased nuclear size and centromere intensity relative to parent cells after nuclear hybridization (Figure II or FIG. 16, B-F). Collectively, CCs represent a novel stem cell population where increased DNA content does not negatively impact on survival or proliferation after induced cell fusion.

CardioChimeras Exhibit Increased Basal Level Expression of Cardiomyogenic Commitment Markers MSCs and CC1 are low to negative for the stem/progenitor cells marker c-kit+, while CC2 and CPCs maintain 20% and 50% c-kit positivity respectively (Figure IIIA of Example 2, or FIG. 17A). Gap junction marker connexin43 and platelet endothelial cell adhesion molecule (pecam or cd31) mRNA are modestly upregulated in CC2 at basal levels (Figure III, B and C). MSCs express high levels of endothelial and smooth muscle markers as indicated by cd31 and smooth muscle 22 (sm22) gene expression (Figure III, C and D)[20]. Although sm22 was not upregulated in CCs, co-incubation of CPCs with MSCs at a 1:1 ratio increased mRNA expression of sm22 (Figure IIID) Interestingly, CC1 has increased mRNA for cardiac troponin T (cTNT or tnnt3) (Figure IIIE) Analysis of basal cardiomyogenic activity further confirmed the identification of CC1 and CC2 after cell fusion. CC1 has increased cardiogenic potential based on expression of cTNT, which corresponds to the lack of c-kit expression. CC2 retains low levels of c-kit expression but has increased expression of endothelial markers, a phenotype that has previously been reported to improve the regenerative capacity of CPCs[2].

CardioChimeras Promote Cardiomyocyte Growth after In Vitro Co-Culture

In order to test the beneficial effects mediated by CCs and parental cells before in vivo cell transfer, neonatal rat cardiomyocytes (NRCMs) were co-incubated with stem cell groups (CPC, MSCs, CPC+MSC, CC1 and CC2) at a ratio of 1:10 in serum depleted conditions. NRCMs maintained in low serum conditions (0.5%) resulted in smaller cardiomyocytes relative to NRCMs maintained in high serum conditions (10%) (FIGS. 2, A, B and G). Addition of MSCs, CPC+MSC, CC1 or CC2 to low serum treated NRCMs significantly increased cardiomyocyte size within 24 hours (FIGS. 2, C-E and G), but CPCs could not induce significant growth of NRCMs (FIGS. 2, F and G). Slow twitch fl-myosin heavy chain (mhy7) over fast twitch α-myosin heavy chain (mhy6) gene expression was not significantly elevated in cardiomyocytes after 24 hours co-incubation with stem cell groups but is highly expressed in low serum conditions indicating that the addition of stem cells does not induce a maladaptive hypertrophic response in cardiomyocytes (FIG. 2H). Regardless of the stem cell population added to cardiomyocytes, NRCMs were protected from cell death based on flow cytometric analysis of apoptotic and necrotic markers (FIG. 2I). With the addition of CC1 and CC2, NRCMs had increased mRNA for stromal derived factor-1 (sdf-1) (FIG. 2J) a cardioprotective cytokine and homing ligand for C—X—C chemokine receptor type 4 (CXCR-4) positive stem cells[21].

CardioChimeras have Increased Gene Expression of Commitment and Paracrine Markers after In Vitro Co-Culture with Cardiomyocytes After co-culture with cardiomyocytes, sm22 was not significantly upregulated in CC groups (FIG. 2K). However, CPC+MSC and CC2 displayed the largest induction of endothelial marker expression pecam, whereas CC2 induced cTNT gene expression after 7 days of co-culture with NRCMs (FIGS. 2, L and M). Paracrine factors are routinely touted as a mechanism for cardioprotection[22], therefore we analyzed our stem cells for expression of growth and immunomodulatory factors. Gene and protein expression for Interleukin-6 (IL-6) is upregulated in CC2 after 24-hour incubation with serum starved NRCMs (FIGS. 2, N and O). Early release of immunomodulatory factors such as IL-6 after acute cardiac damage has been shown to have anti-apoptotic properties[23]. In summary, CC1 shows increased cellular size and expression of early cardiac commitment markers without impairment in cell proliferation. CC2 has similar morphological features to CPCs in addition to having a higher proliferative status relative to CC1. In fact, CC2 was most responsive to differentiation as evidenced by the up regulation of endothelial and cardiac markers in addition to increased expression of the immunomodulatory factor IL-6. This preliminary data further validates the in vivo application of these two distinct cell hybrids.

CardioChimeras Improve Left Ventricular Structure and Cardiac Function after Myocardial Injury To establish the therapeutic efficacy of CCs relative to parent cells or parent cells combined, we injected a total of 100,000 cells in the border zone region of an acutely damaged mouse heart. At 1-week post injury (WPI), all groups had similar reductions in AWT and EF (FIGS. 3, A and D). CC1 and CC2 exhibited increased AWT at 4 WPI, but only CC1 treated hearts preserved AWT up to 18 WPI (FIG. 3A). Heart weight to body weight ratios (HW/BW) at 12 and 18 weeks did not increase in CC treated hearts indicating that hypertrophy was not a contributing factor to increasing AWT (FIGS. 3, B and C). Rather, CC1 hearts had significantly reduced HW/BW relative to vehicle control (PBS) (FIG. 3C). EF was increased in CC1 and CPC+MSC hearts starting at 3 WPI, and CC1 and CC2 had increased EF over PBS at 6 WPI (FIG. 3D). CC and CPC+MSC-treated groups exhibited improved EF starting at 12 WPI, whereas the CPC treatment was beneficial for cardiac function only at 18 WPI (FIG. 3D). Correlating with improved EF, CC1 treatment significantly improved positive developed pressure over time (dP/dT) (FIG. 3E) and negative dP/dT (FIG. 3F). CC1, CC2, CPC+MSC and CPC hearts had smaller infarct sizes relative to PBS (FIG. 3G). MSC groups exhibited increased infarct size when measuring scar between 4 and 12 WPI, CPC and CPC+MSC hearts remain unchanged, and CC1 and CC2 treatment reduced infarct size as represented by Masson's Trichrome staining (FIG. 3, G-N).

Cellular Engraftment of CardioChimeras 4 Weeks after Damage

Scar size measured at 4 WPI was not significantly different among infarcted heart groups (Figure IV or FIGS. 18, A and B-E). Next, we were interested in determining cell persistence at this time point and were able to detect CPCs labeled with mcherry in CPC alone and CPC+MSC treated hearts (Figure IV or FIGS. 18, F and G). Interestingly, mcherry$^+$ CPCs were detected near small c-kit$^+$/cTNT$^+$ cardiomyocytes in the infarct area (Figure IVH). CC1 detected by both GFP and mcherry expression did not display evidence of commitment at this early time point (Figure IV, I-K).

CardioChimeras have Increased Engraftment, Expression of Cardiomyogenic Markers and Support the Increased Presence of c-Kit Positive Cells in the Myocardium 12 Weeks after Damage C-kit$^+$ cell recruitment in damaged regions supports endogenous differentiation and myocardial repair[22]. Although infarction sizes were similar at the 4-week time point, induction of endogenous c-kit cells in the infarcted area was increased in MSC, CPC+MSC, and CC1 treated hearts (FIG. 4, A-C). At 12 WPI, a high number of c-kit$^+$ cells were observed in PBS and MSC treated hearts, yet c-kit$^+$ cells remained visually present in CPC+MSC, CC1 and CC2 treated hearts surrounding mcherry$^+$ cells in the border zone regions (FIG. 4, D-G). The percentage of cell engraftment was increased in CC1 and CC2 hearts at 1.9% and 1.1% respectively relative to 0.21% and 0.29% in CPC and CPC+MSC hearts (FIGS. 4, H and K-O). MSCs were detected at a much lower level or 0.04% of the total left ventricular free wall (FIGS. 4, H, I and J). CPCs discovered in the border zone areas co-expressed c-kit and mcherry in CPC hearts and expressed mcherry alone in CPC+MSC hearts (FIGS. 4, K and L). CC1 and CC2 had increased levels of engraftment, expressed cTNT and were surrounded by endogenous c-kit$^+$ cells (FIG. 4, M-O).

CardioChimeras Increase Capillary Density in the Infarct Area

Capillary density was measured in the border zone and infarcted areas at 12 WPI. Shams, non-injured controls, are included as a standard for capillary density compared to injured hearts (FIGS. 5, A, B and C). Parent cells, individual or combined, or CC treatment did not significantly increase capillary density in the border zone regions relative to PBS (FIGS. 5, A and C-I). MSC, CPC or CPC+MSC treated hearts similarly did not affect the number of capillaries discovered in the infarct zone (FIGS. 5, B and J-M). Notably, CC1 and CC2 treated hearts had significant increases in isolectin$^+$ structures in the infarct regions at 12 WPI (FIGS. 5, B and N-O).

CPC, MSC and CardioChimera Treatment Antagonizes Cardiomyocyte Hypertrophy in the Remote Region and Preserves Cardiomyocyte Size in the Infarcted Regions Cellular treatment and long term engraftment of cells is reported to induce compensatory hypertrophy in areas of damage preventing progression of heart failure after MI[24]. MSC and vehicle treated hearts showed increased cardiomyocyte size in the remote area relative to sham (FIGS. 6, A and C-E). CPC+MSC, CC1 and CC2 treated hearts maintained cardiomyocyte size in the remote region similar to non-injured controls (FIGS. 6, A, C and G-I). Although stem cell treatments could not modify border zone cardiomyocyte size (Figure V or FIG. 19, A-G), injection of CPC, CPC+MSC, and both CCs increased cardiomyocyte size in the infarcted regions relative to PBS and MSC treated hearts up to 12 WPI (FIGS. 6, B and J-O). This data indicates that improved engraftment of stem cells correlates with the presence of microvascular structures and preservation of cardiomyocyte size in the remote and infarct regions relative to failing and severely damaged hearts.

Discussion

In this report, we demonstrated a novel approach by using cell fusion to enhance delivery of novel and unique stem cell properties created within a single cell. Cardiac-derived CPCs and bone marrow derived MSCs were chosen for this study as both of these cell types have established roles in the heart: CPCs contribute to direct cardiomyogenic differentiation whereas MSCs provide for protective immunomodulatory and growth factor paracrine secretion[4, 9]. CCs injected into the acutely damaged heart improved structural integrity and reduced infarct size (FIG. 3). Furthermore, functional improvements were observed in CC treated hearts, and increased engraftment was apparent in the border zones after 12 WPI (FIGS. 3 and 4). Specifically, CC1 significantly improved myocardial wall structure compared to control groups, and both CC1 and CC2 showed increased cellular engraftment in the border zone regions corresponding to a reduced infarct size and preservation of vascular structures in the neighboring infarct (FIGS. 3, 4 and 5). Notably, CCs improved EF earlier in the assessment (6 WPI) relative to combined and single cell injections (FIG. 3). At 12 WPI, CC therapy promoted increases in cardiac function, induction of endogenous c-kit cells and maintenance of cardiomyocyte size that were comparable to mixed cell injections (FIGS. 3, 4 and 6). Initial improvements in cardiac function are most likely mediated by the combination of increased cell persistence and growth factor secretions conferred by CCs supporting long-term vascular stability and mitigation of adverse scar remodeling that is improved over combined therapy of CPCs and MSCs (FIGS. 3 and 5).

BMCs, the most common stem cell for cardiac therapy, apparently undergo engraftment through a combination of cell fusion and to a lesser degree by direct transdifferentiation events[25]. Membrane fusion is dependent upon signaling mechanisms involving paxillin induced focal adhesions and recycling of integrins as demonstrated between macrophages and myoblasts[26]. In the heart, cell fusion is increased between exogenous stem cells and apoptotic cardiomyocytes similar to enhanced myoblast fusion in the presence of phosphatidylserine presenting cells[14, 27]. Altered DNA content has been raised as an issue following fusion events as genomic instability leads to cellular aging[28]. Somatic cells exhibiting chromosomal mosaicism such as through the loss or deletions of chromosomes do not significantly affect stem cell properties or cell fate[29]. As a result, CCs do not appear transformed but rather retain properties of CPCs and MSCs to support enhanced myocardial repair. To this effect, we were interested in correlating the in vitro properties of CC1 and CC2 to the observed effects in the myocardium. Although, both CC1 and CC2 were responsive to co-culture with cardiomyocytes (FIG. 2), CC treated hearts showed only a modest up regulation of cTNT in vivo (FIG. 4). CC1 in culture did not undergo significant cardiomyogenic commitment or secrete IL-6, yet CC1 hearts had stabilized AWT (FIG. 3). We hypothesize that the larger cell body of CC1 contributed to higher rates of engraftment contributing to the improvement in myocardial structure without significant evidence of cardiogenic commitment (FIGS. 1 and 4). Prior to injection, CC2 exhibited a predominately CPC phenotype, and supported in vivo effects such as enhanced persistence and increased cardiac function similar to CC1 and CPC+MSC treated hearts. We propose that the high proliferative capacity of CC2 and expression of immunomodulatory factor IL-6 contributed to structural and functional benefits but through the contribution of distinct phenotypic characteristics from CC1 and CC2 respectively.

Figure 17:
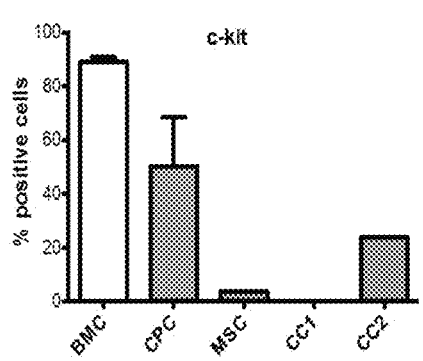
FIG. 17A-E graphically illustrates that CardioChimeras have increased expression of cardiomyogenic commitment markers at basal levels.
Figure 17:
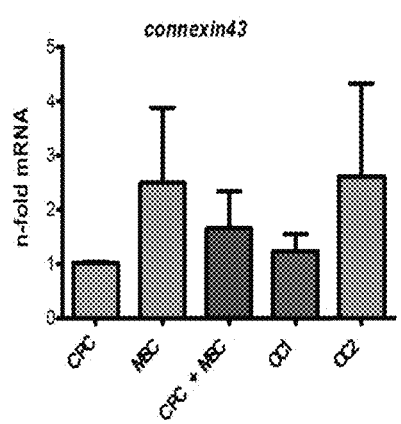
Figure 17:
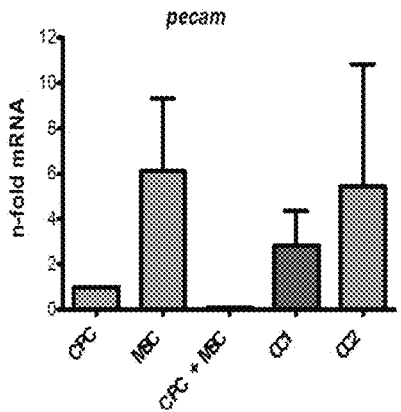
Figure 17:
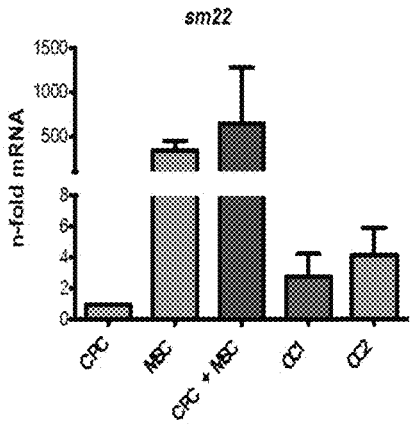
Figure 17:
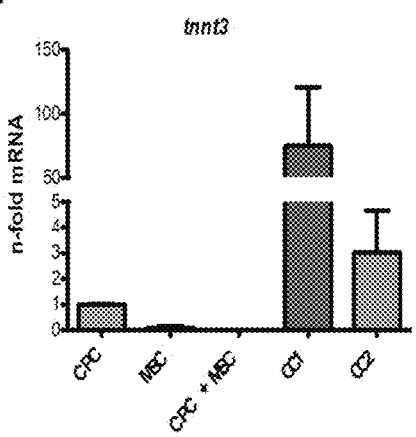

Increased basal expression of cardiomyogenic factors was observed in CCs (Figure III of Example 2, or FIG. 17). Pre-committed cells, but not fully mature stem cell derived cardiomyocytes improve exogenous cell coupling and formation of gap junction proteins[30]. CCs display coordinated phenotypic properties of commitment and increased paracrine abilities to promote cardiomyocyte health much like the MSC parent and CPC+MSC parents combined (FIG. 2). Factor(s) that promote growth of cardiomyocytes and stabilization or the creation of microvasculature (FIGS. 5 and 6) remain to be established in our model of mouse CCs, but is certainly a subject of future investigations. Gene dosage effects as well as modifying the ratio of cell numbers before cell fusion leads to unique phenotypic properties such as proliferation and inhibition of senescence[31-33]. Embryonic stem cell (ESC) fusion with somatic cells facilitates reprogramming using equal cellular ratios indicating that ESCs are the more dominant cell type[34]. In this report, the CPC parent phenotype dominates in the fused progeny and most likely mediates early cardiomyogenic factors in CCs, whereas paracrine mediated effects from the MSC parent is secondary. For future studies, selecting the optimal cells and gene dosage for fusion will allow us to more effectively design hybrids for stronger traits towards commitment or paracrine effects.

Therapeutic delivery of MSCs improves cardiac function and structure mainly through paracrine mediated effects. Secretion of factors such as SDF-1 and IGF-1 support endogenous recruitment of c-kit+ progenitor cells and further facilitates cardiomyocyte cell cycle entry and survival[35-37]. Immunomodulatory functions of MSCs to inhibit excess scar formation is an attractive therapy for several disease states[38]. In this study, MSC treatment was unable to prevent increases in scar size or decreases in cardiac function up to 18 weeks similar to the deteriorating PBS treated hearts. Although, MSC addition did maintain size and survival of the responding cardiomyocytes, these beneficial effects were not recapitulated in vivo after MSC transfer (FIGS. 2 and 3). Apoptosis and slow proliferation rate are likely contributing factors to the disappearance of MSCs at later time points (FIGS. 1 and 4). Instead, MSC and PBS treated hearts sustained increases in c-kit+ cells, which are most likely increased through chronic inflammation and recruitment of hematopoietic derived c-kit+ mast cells (FIG. 4)

The optimal cell number chosen for therapy is a critical aspect to promote structural and functional recovery after MI. Delivery of human CPC+MSC in a pig model of ischemia resulted in positive remodeling and engraftment using 200-fold more MSCs relative to CPCs[11]. For our study, we placed CPCs to MSCs at a one-to-one ratio as the appropriate control compared to our CCs. The engraftment efficiency of MSCs could have been greatly limited from the beginning of the experiment due to reduced MSC cell numbers (FIG. 4). Benefits of co-culture of CPCs with MSCs are consistent with previous findings as MSC co-incubation with CPCs at equal ratios increased basal differentiation markers such as sm22, which was not observed in CCs (Figure III of Example 2, or FIG. 17). Furthermore, during co-culture with NRCMs, CPC+MSC groups exhibited increased cardiomyogenic markers sm22, pecam and cTNT (FIG. 2). It remains unclear if differentiation resulted from CPCs alone in culture with MSCs, although significant cell death of MSCs alone was observed when co-cultured with NRCMs for seven days. The comparatively modest therapeutic benefit of unmodified CPCs has been previously shown from our laboratory[2, 3]. Clearly, pinpointing the mechanistic contribution of MSCs to support CPCs in our CPC+MSC treated hearts is an important unanswered question to be resolved in future investigations.

Although engraftment efficiency of CPCs co-injected with MSCs was not significantly improved relative to CPC hearts alone, function was improved in CPC+MSC hearts at a much earlier time point. We can hypothesize that MSCs in the acute stages of damage (<4 weeks) facilitated protective endogenous cell reprogramming without long-term persistence, which was not sufficient to impact on exogenous CPC proliferation and/or engraftment, consistent with reports from other groups[10].

From the numerous cell types touted to be efficacious for cardiac clinical therapy, CPCs and MSCs are particularly promising because of established protocols for cell isolation and expansion in clinical settings[6, 8]. Although MSCs show much lower rates of persistence in the damaged heart than CPCs, cell therapeutic practices could benefit from investigation of how to enhance immunomodulatory effects of MSCs[9]. Currently, "Off-the-shelf" allogeneic cellular options include cardiosphere derived cells and MSCs that may exert beneficial effects after MI but suffer from poor persistence following delivery[8, 39]. In comparison, ESCs and induced pluripotent stem cells exhibit extended proliferation and are less prone to immuno rejection and/or cell senescence after transplantation[40]. However, ESCs have reduced capacity for integrative cardiomyogenesis as demonstrated by arrhythmogenic events in large animal models[41]. Our cell fusion approach aims to capitalize on adult stem cells that have validated cardiac therapeutic effects in order to create an exceptional composite hybrid with anti-inflammatory functions arising from the inclusion of allogeneic MSCs. Transplanted MSCs have suggested immunomodulatory functions by regulation of immune cells in the damaged setting. Mechanistically, MSCs have the potential to balance the inhibition of T cell proliferation by secretion of indoleamine and promotion of dendritic cell differentiation into T regulatory cells by secretion of IL-6 and interleukin-10 making this cellular source an essential component of future cardiac stem cell hybrids[42]. Additionally, fusion of aged stem cells with more youthful cells could confer cell rejuvenation and reverse signs of cellular aging[33, 43] In the era of human cord blood banking, the isolation of immunoprivileged stromal cells from the same patient can be easily fused with stem cells harboring tissue specific regenerative capacity, resulting in a novel cell type that is resistant to rejection in addition to having desired cellular effects such as proliferation and direct tissue commitment. From a translational perspective, cell fusion is an adaptable genetic engineering strategy that qualitatively enhances adult stem cell properties such as persistence, anti-inflammatory and growth factor secretion and direct cardiomyogenesis to sustain long-term cardiac repair.

FIGURE LEGENDS

Example 2

FIG. 9 illustrates Phenotypic Characterization of CardioChimeras. (A) Schematic representation of the creation of CardioChimeras. (B) Proliferation of CCs, CPCs and MSCs represented as a fold change relative to day of plating. (C) Cell doubling time in hours. (D) Cell death assay of CCs and parents cells after treatment with 40 µM or 80 µM hydrogen peroxide represented as a fold change relative to cells not treated with hydrogen peroxide. (E) p16 and (F) p53 gene expression normalized to ribosomal 18s and represented as a fold change relative to CPCs. (G) Cell surface area represented as a fold change normalized to CPCs (blue dashed line, 1.0). Fluorescent images of (H) CPCs, (I) MSCs, (J) CC1 or (K) CC2. * $p<0.05$,  $p<0.01$, * $p<0.001$. Scale bar is 40 µm.

Figure 10:
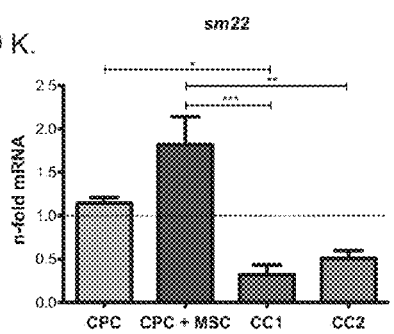
Figure 10:
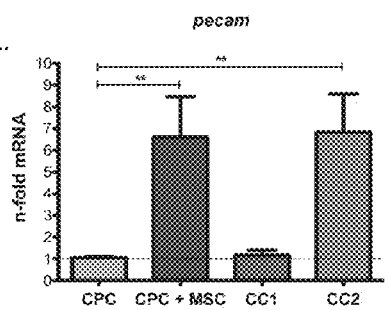
Figure 10:
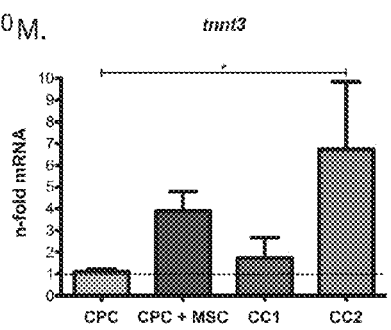
Figure 10:
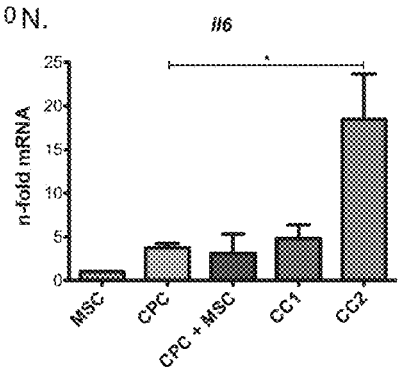
Figure 10:
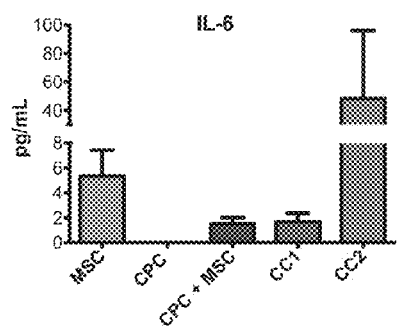

FIG. 10 illustrates that CardioChimeras promote cell growth and have increased commitment and paracrine gene expression after in vitro co-culture with cardiomyocytes. (A) NRCMs in low serum. (B) NRCMS in high serum. (C) NRCMs in low serum and after the addition of MSCs, (D) CC1, (E) CC2 or (F) CPCs for 24 hours. Cardiomyocytes were visualized by staining with sarcomeric actinin. TO-PRO-3 iodide was used to visualize nuclei. (G) Quantitation of cardiomyocyte size. (H) Gene expression of mhy7 over mhy6 represented as a fold change relative to high serum. (I) Cardiomyocyte cell death. Values are represented as fold change of Annexin $V^+$ and Sytox Blue$^+$ cells relative to high serum. (J) sdf-1 gene expression in cardiomyocytes alone after the addition of stem cells. (K-M) Gene expression in stem cells after a 7-day co-culture with NRCMs. (K) sm22 (L) pecam gene expression. (M and N) il6 gene expression analyzed in stem cells after a 24-hour co-culture with NRCMs. (O) IL-6 expression confirmed by ELISA. (G-J) Statistical values were determined by one-way ANOVA compared to low serum controls. * $p<0.05$,  $p<0.01$, * $p<0.001$. Scale bar is 40 µm.

Figure 11:
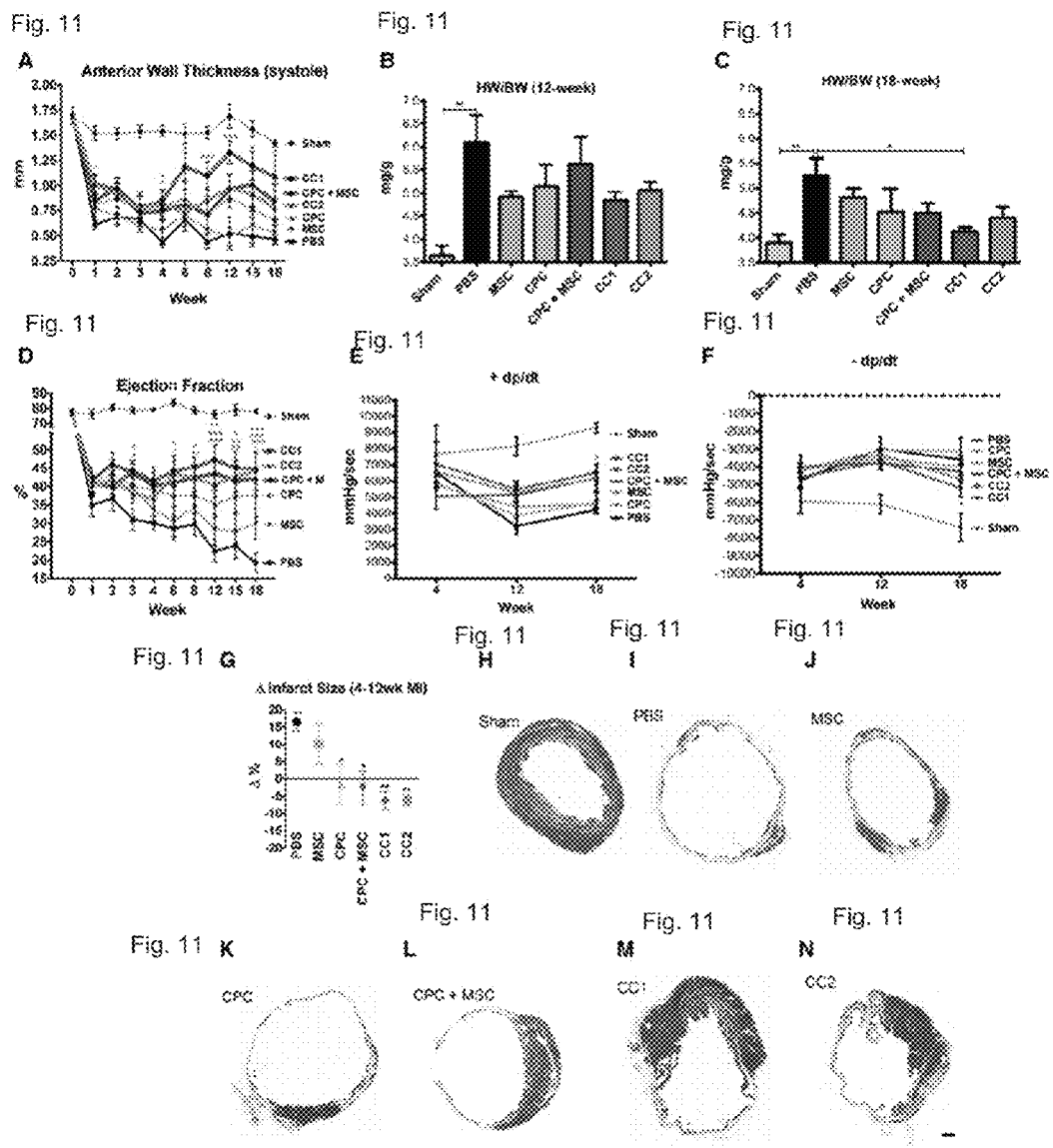

FIG. 11 illustrates that CardioChimeras improve left ventricular wall structure and cardiac function after myocardial injury. (A) Longitudinal assessment of anterior wall thickness during systole (mm) over 18 weeks. (B) Heart weight to body weight ratio (mg/g) at 12 WPI (C) 18 WPI. Sample sizes of 3-5 mice per group. (D) Longitudinal assessment of ejection fraction (%). (E) Positive and (F) Negative developed pressure over time represented as mmHg/sec at 4, 12 and 18 WPI. (G) Change in infarct size between 4 and 12 weeks time points. P values were determined by one-way ANOVA compared to PBS treated controls. (H-N) Masson's Trichrome staining and representative images of infarct size and fibrosis in (H) Sham, (I) PBS, (J) MSC, (K) CPC, (L) CPC+MSC, (M) CC1 and (N) CC2. All statistical values were determined by two-way ANOVA compared to PBS treated hearts. * $p<0.05$,  $p<0.01$, * $p<0.001$. Colors of asterisk(s) correspond to heart group. Scale bar is 250 µm.

Figure 12:
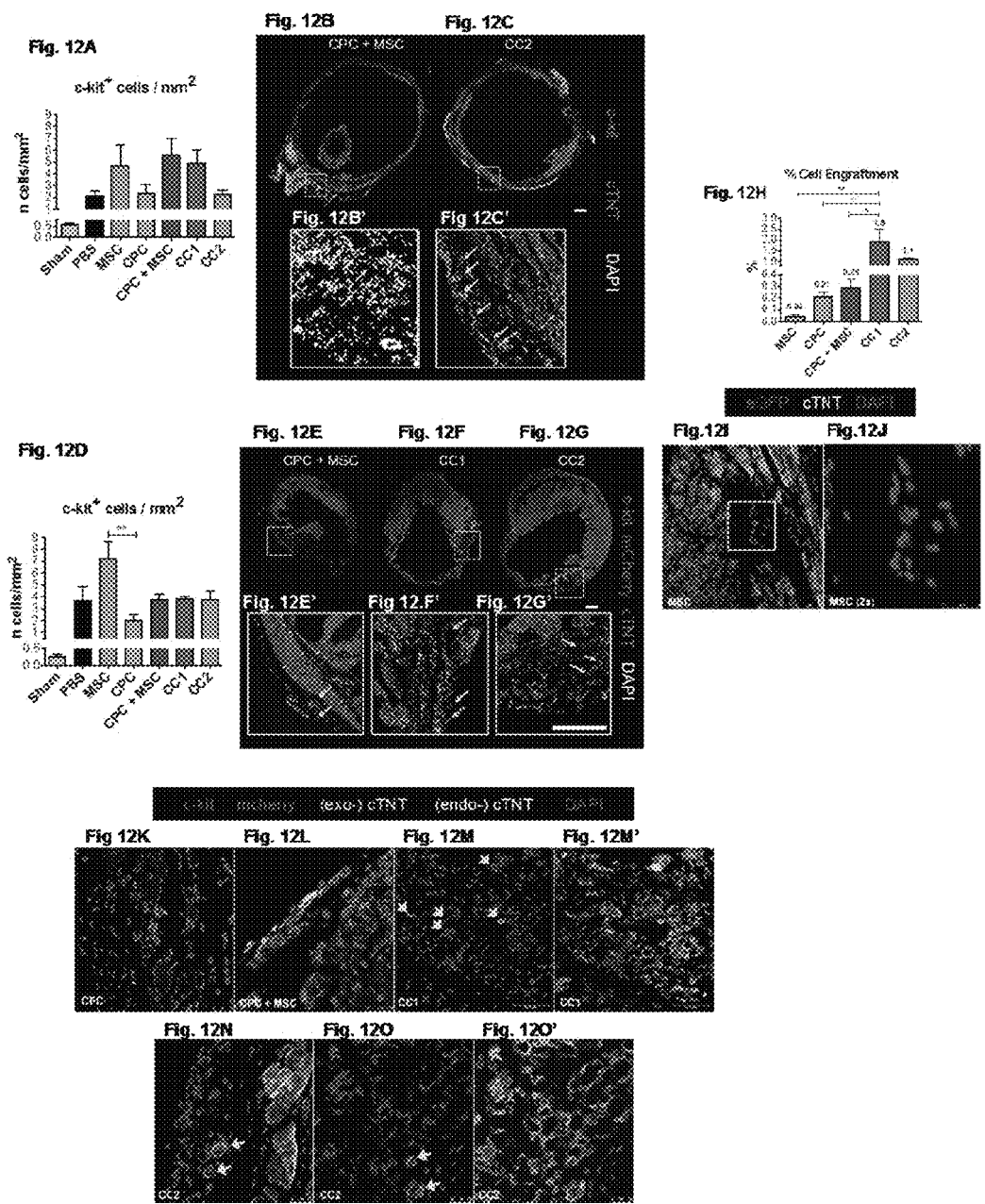

FIG. 12 illustrates that CardioChimeras have increased engraftment, expression of cardiomyogenic markers and support the increased presence of c-kit$^+$ cells in the myocardium 12 weeks after damage. (A) Number of c-kit$^+$ cells over the area of left ventricular free wall (mm$^2$) in a 4-week damaged heart. Representative whole heart scans of (B) CPC+MSC and (C) CC2 treated hearts to visualize c-kit$^+$ cells (red). Scale bar is 100 µm. (B) and (C)C-kit$^+$ cells are identified by yellow arrows. Scale bar is 50 µm. (D) Number of c-kit$^+$ cells in 12-week damaged heart. Representative whole heart scans of (E) CPC+MSC, (F) CC1 and (G) CC2 treated hearts to visualize exogenous mcherry$^+$ cells (green) and c-kit$^+$ cells (red). Scale bar is 100 µm. (E), (F) and (G)C-kit$^+$ cells are identified by yellow arrows. Scale bar is 100 µm. (H) Cell engraftment efficiency (%). (I) MSC detected by GFP fluorescence at 12 weeks. (J) 2× zoom of a MSC in the border zone area. (K) C-kit$^+$/mcherry$^+$ CPCs in the border zone area. (L) Mcherry$^+$ CPC in CPC+MSC treated heart. (M) Mcherry$^+$ CC1 visualized in the infarcted area surrounded by c-kit$^+$ cells (green). (M') Overlay of cTNT (exogenous-cTNT, yellow) in CC1 mcherry labeled cells. (N) Mcherry$^+$ CC2 visualized in the infarcted area surrounded by c-kit$^+$ cells (green). (O) Mcherry$^+$ CC2 (red) visualized in the infarcted area surrounded by c-kit$^+$ cells (green). (O) Overlay of cTNT (exogenous-cTNT, yellow) in CC2 mcherry labeled cells. Endogenous-cTNT (white) labels existing cardiomyocytes. Sample size of 3 mice per group. * $p<0.05$,  $p<0.01$, * $p<0.001$.

Figure 13:
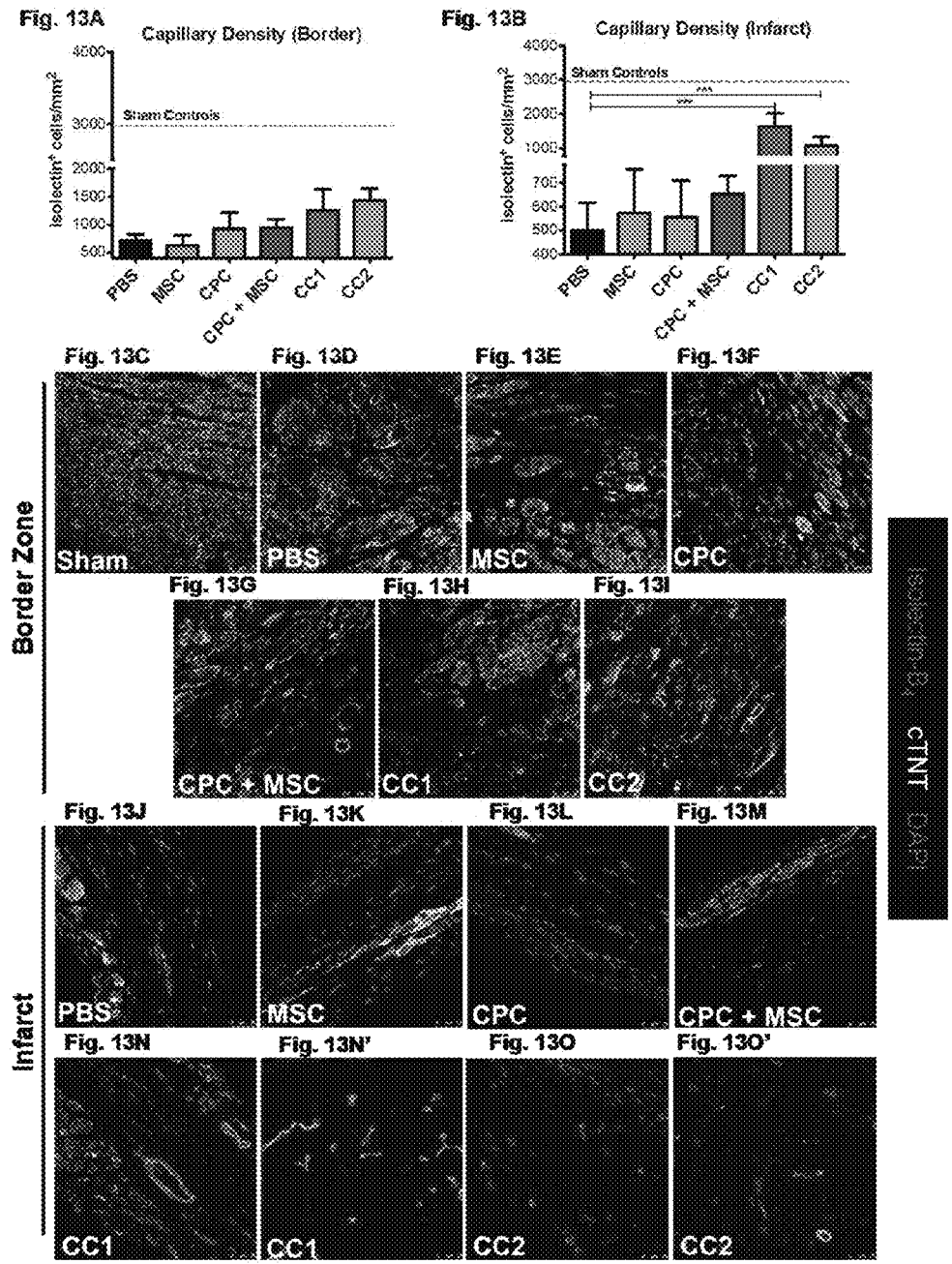

FIG. 13 illustrates that CardioChimeras increase capillary density in the infarct area. (A) Capillary density in the border zone and (B) Infarcted heart regions. Sample sizes are 3-4 mice per group. Sham controls (dashed line) are represented as control for baseline density of isolectin$^+$ structures per mm$^2$. (C-I) Representative border zone images to visualize isolectin$^+$ structures. (J-O) Representative infarct zone images to visualize and quantitate isolectin$^+$ structures. Green=Isolectin B4, White=cardiac troponin T and Blue=DAPI to stain for nuclei. Scale bar is 25 µm. * $p<0.05$,  $p<0.01$, * $p<0.001$.

Figure 14:
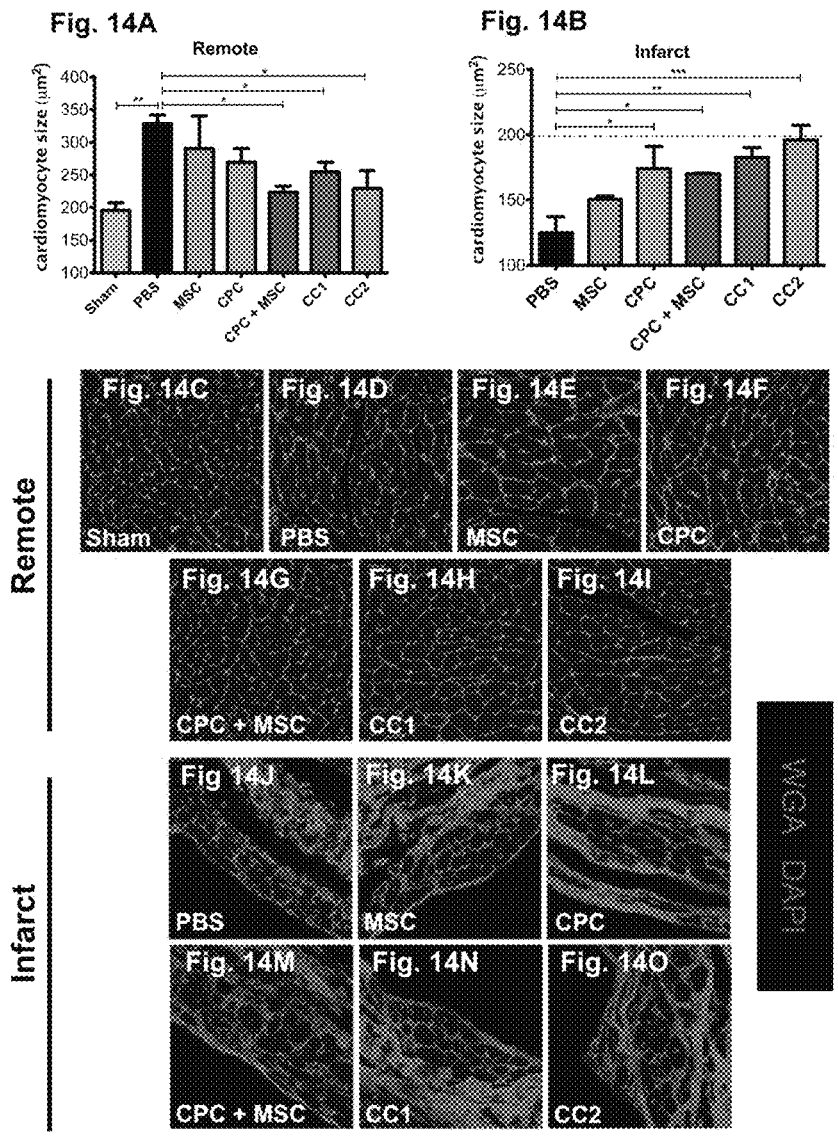

FIG. 14 illustrates that CPC, MSC and CardioChimera treatment antagonizes cardiomyocyte hypertrophy in the remote region and preserves cardiomyocyte size in the infarcted regions. (A) Mean cardiomyocyte size in the remote and (B) Infarct regions. Sample size is 3-4 mice per group. (C-I) Representative images of remote area cardiomyocyte size. (J-O) Representative images of infarct area cardiomyocytes. Red=Wheat germ agglutinin, White=cardiac troponin T and Blue=DAPI to stain for nuclei. Scale bar is 25 µm. * $p<0.05$,  $p<0.01$, * $p<0.001$.

FIG. 15 illustrates Phenotypic Characterization of CardioChimera clones. (A) Proliferation data for the 18 CardioChimera clones relative to day of plating using a direct-fluorescent based assay (CyQuant Assay). CardioChimeras are categorized as slow (blue), slow-medium (orange), medium-fast (red) and fast (green) growing. Experimental control groups (CPC, MSC and CPC+MSC) cell lines are represented as dashed bold lines. CardioChimera 1 and 2 are represented as solid bold lines. (B) CardioChimera death after treatment with hydrogen peroxide stimulus. Values are represented as a fold change of Annexin $V^+$ and Sytox Blue$^+$ compared to cells in growth media alone. (C) Neonatal rat cardiomyocytes incubated in high or low serum or with the addition of parent cells, parent cells combined or CardioChimeras. (D) Cell death was quantitated by measuring a fold change of Annexin V+ and Sytox Blue+ cardiomyocytes relative to cardiomyocytes in high serum. (E) Cardiomyocyte size was quantitated in high serum or with the addition parent cells, parent cells combined or CardioChimeras.

FIG. 16 illustrates that CardioChimeras have increased nuclear size and DNA content. (A) Detailed protocol for the fusion and clonal expansion of CardioChimeras. Briefly, mouse CPCs were co-incubated with mouse MSCs at a 1:1 ratio with addition of Sendai virus. Cells were centrifuged to force cell contact and single cell sorted based on fluorescent expression of mcherry and GFP. Clones were confirmed by flow cytometric analysis. (B) Measurement of nuclear size and (C) Centromere intensity in parent MSCs, CC2 and CC1. (D) Representative images of nuclei in parent (E) CC2 and (F) CC1. Blue represents DAPI staining of DNA content and red represents centromere probe binding. Scale bar is 20 μm. * $p<0.05$,  $p<0.01$, * $p<0.001$.

FIG. 17 illustrates that CardioChimeras have increased expression of cardiomyogenic commitment markers at basal levels. (A)C-kit protein expression as analyzed by flow cytometry. C-kit purified bone marrow cells were utilized as a positive control. (B) connexin 43, (C) pecam (cd31), (D) sm22 and (E) cTNT (tnnt3) gene expression was analyzed by qRT-PCR in CPC, MSC, CPC+MSC, CC1 and CC2 after normalization to ribosomal 18s. Values are represented as a fold change relative to CPCs.

FIG. 18 illustrates Cellular Engraftment of CardioChimeras 4 weeks after damage. (A) Infarct size was not significantly different between infarcted groups (mean=18.23%). N=2-4 per group. (B-E) Masson's Trichrome staining and representative images of (B) PBS, (C) CPC, (D) CPC+MSC and (E) CC1 hearts to visualize scar size and fibrosis. Scale bar is 250 μM. (F) Mcherry+ CPCs detected in the infarct area in CPC treated hearts. (G) Mcherry+ CPCs detected in the infarct area in CPC+MSC treated hearts. (H) Mcherry+ CPCs adjacent to c-kit+/cTNT+ cardiomyocytes in CPC+MSC treated hearts. (I) and (J) CC1 expressing eGFP and mcherry in the infarcted area. (K) 2× zoom of CC1. Scale bar is 25 μm for confocal images. Scale bar is 50 μm in (G).

FIG. 19 illustrates Cardiomyocyte size is unaffected in the border zone region after treatment. (A) Mean cardiomyocyte size in the border zone regions. Sample size is 3-4 mice per group. (B-G) Representative images of border zone area cardiomyocytes. Red=Wheat germ agglutinin, White=cardiac troponin T and Blue=DAPI to stain for nuclei. Scale bar is 25 μm. * $p<0.05$,  $p<0.01$, * $p<0.001$.

FIG. 20 illustrates Table I: Phenotypic characterization of the 18 CardioChimeras. Individual clones were analyzed for phenotypic properties such as proliferation, cell death and and cell surface area and potential for paracrine mediated effects on cardiomyocytes (Cardiomyocyte growth and Cardiomyocyte Death). The last panel specifies exclusion reason(s).

FIG. 21 illustrates Table II, describing the antibodies used in the study of Example 2.

REFERENCES

Example 2

1. Hong K U, Guo Y, Li Q H, Cao P, Al-Maqtari T, Vajravelu B N, Du J, Book M J, Zhu X, Nong Y, Bhatnagar A, Bolli R. C-kit+ cardiac stem cells alleviate post-myocardial infarction left ventricular dysfunction despite poor engraftment and negligible retention in the recipient heart. *PLoS One.* 2014; 9:e96725
2. Fischer K M, Cottage C T, Wu W, Din S, Gude N A, Avitabile D, Quijada P, Collins B L, Fransioli J, Sussman M A. Enhancement of myocardial regeneration through genetic engineering of cardiac progenitor cells expressing pim-1 kinase. *Circulation.* 2009; 120:2077-2087
3. Mohsin S, Khan M, Toko H, Bailey B, Cottage C T, Wallach K, Nag D, Lee A, Siddiqi S, Lan F, Fischer K M, Gude N, Quijada P, Avitabile D, Truffa S, Collins B, Dembitsky W, Wu J C, Sussman M A. Human cardiac progenitor cells engineered with pim-i kinase enhance myocardial repair. *Journal of the American College of Cardiology.* 2012; 60:1278-1287
4. Leri A, Kaj stura J, Anversa P. Cardiac stem cells and mechanisms of myocardial regeneration. *Physiological reviews.* 2005; 85:1373-1416
5. van Berlo J H, Kanisicak O, Maillet M, Vagnozzi R J, Karch J, Lin S C, Middleton R C, Marban E, Molkentin J D. C-kit+ cells minimally contribute cardiomyocytes to the heart. *Nature.* 2014; 509:337-341
6. Bolli R, Chugh A R, D'Amario D, Loughran J H, Stoddard M F, Ikram S, Beache G M, Wagner S G, Leri A, Hosoda T, Sanada F, Elmore J B, Goichberg P, Cappetta D, Solankhi N K, Fahsah I, Rokosh D G, Slaughter M S, Kaj stura J, Anversa P. Cardiac stem cells in patients with ischaemic cardiomyopathy (scipio): Initial results of a randomised phase 1 trial. *Lancet.* 2011; 378:1847-1857
7. Sanganalmath S K, Bolli R. Cell therapy for heart failure: A comprehensive overview of experimental and clinical studies, current challenges, and future directions. *Circ Res.* 2013; 113:810-834
8. Hare J M, Fishman J E, Gerstenblith G, DiFede Velazquez D L, Zambrano J P, Suncion V Y, Tracy M, Ghersin E, Johnston P V, Brinker J A, Breton E, Davis-Sproul J, Schulman I H, Byrnes J, Mendizabal A M, Lowery M R, Rouy D, Altman P, Wong Po Foo C, Ruiz P, Amador A, Da Silva J, McNiece I K, Heldman A W, George R, Lardo A. Comparison of allogeneic vs autologous bone marrow-derived mesenchymal stem cells delivered by transendocardial injection in patients with ischemic cardiomyopathy: The poseidon randomized trial. *Jama.* 2012; 308:2369-2379
9. Wang Y, Chen X, Cao W, Shi Y. Plasticity of mesenchymal stem cells in immunomodulation: Pathological and therapeutic implications. *Nature immunology.* 2014; 15:1009-1016
10. Hatzistergos K E, Quevedo H, Oskouei B N, Hu Q, Feigenbaum G S, Margitich I S, Mazhari R, Boyle A J, Zambrano J P, Rodriguez J E, Dulce R, Pattany P M, Valdes D, Revilla C, Heldman A W, McNiece I, Hare J M. Bone marrow mesenchymal stem cells stimulate cardiac stem cell proliferation and differentiation. *Circ Res.* 2010; 107:913-922
11. Williams A R, Hatzistergos K E, Addicott B, McCall F, Carvalho D, Suncion V, Morales A R, Da Silva J, Sussman M A, Heldman A W, Hare J M. Enhanced effect of combining human cardiac stem cells and bone marrow mesenchymal stem cells to reduce infarct size and to restore cardiac function after myocardial infarction. *Circulation.* 2013; 127:213-223
12. Alvarez-Dolado M, Pardal R, Garcia-Verdugo J M, Fike J R, Lee H O, Pfeffer K, Lois C, Morrison S J, Alvarez-Buylla A. Fusion of bone-marrow-derived cells with purkinje neurons, cardiomyocytes and hepatocytes. *Nature.* 2003; 425:968-973

13. Johansson C B, Youssef S, Koleckar K, Holbrook C, Doyonnas R, Corbel S Y, Steinman L, Rossi F M, Blau H M. Extensive fusion of haematopoietic cells with purkinje neurons in response to chronic inflammation. *Nature cell biology.* 2008; 10:575-583
14. Yang W J, Li S H, Weisel R D, Liu S M, Li R K. Cell fusion contributes to the rescue of apoptotic cardiomyocytes by bone marrow cells. *Journal of cellular and molecular medicine.* 2012; 16:3085-3095
15. Soza-Ried J, Fisher A G. Reprogramming somatic cells towards pluripotency by cellular fusion. *Curr Opin Genet Dev.* 2012; 22:459-465
16. Tsubouchi T, Soza-Ried J, Brown K, Piccolo F M, Cantone I, Landeira D, Bagci H, Hochegger H, Merkenschlager M, Fisher A G. DNA synthesis is required for reprogramming mediated by stem cell fusion. *Cell.* 2013; 152:873-883
17. Acquistapace A, Bru T, Lesault P F, Figeac F, Coudert A E, le Coz O, Christov C, Baudin X, Auber F, Yiou R, Dubois-Rande J L, Rodriguez A M. Human mesenchymal stem cells reprogram adult cardiomyocytes toward a progenitor-like state through partial cell fusion and mitochondria transfer. *Stem Cells.* 2011; 29:812-824
18. Takei S, Yamamoto M, Cui L, Yue F, Johkura K, Ogiwara N, Iinuma H, Okinaga K, Sasaki K. Phenotype-specific cells with proliferative potential are produced by polyethylene glycol-induced fusion of mouse embryonic stem cells with fetal cardiomyocytes. *Cell Transplant.* 2005; 14:701-708
19. Islam M Q, Meirelles Lda S, Nardi N B, Magnusson P, Islam K. Polyethylene glycol-mediated fusion between primary mouse mesenchymal stem cells and mouse fibroblasts generates hybrid cells with increased proliferation and altered differentiation. *Stem Cells Dev.* 2006; 15:905-919
20. Davani S, Marandin A, Mersin N, Royer B, Kantelip B, Herve P, Etievent J P, Kantelip J P. Mesenchymal progenitor cells differentiate into an endothelial phenotype, enhance vascular density, and improve heart function in a rat cellular cardiomyoplasty model. *Circulation.* 2003; 108 Suppl 1:11253-258
21. Zaruba M M, Franz W M. Role of the sdf-1-cxcr4 axis in stem cell-based therapies for ischemic cardiomyopathy. *Expert opinion on biological therapy.* 2010; 10:321-335
22. Zacchigna S, Giacca M. Extra- and intracellular factors regulating cardiomyocyte proliferation in postnatal life. *Cardiovascular research.* 2014; 102:312-320
23. Fontes J A, Rose N R, Cihakova D. The varying faces of il-6: From cardiac protection to cardiac failure. *Cytokine.* 2015
24. Endo J, Sano M, Fujita J, Hayashida K, Yuasa S, Aoyama N, Takehara Y, Kato O, Makino S, Ogawa S, Fukuda K. Bone marrow derived cells are involved in the pathogenesis of cardiac hypertrophy in response to pressure overload. *Circulation.* 2007; 116:1176-1184
25. Wu J M, Hsueh Y C, Chang H J, Luo C Y, Wu L W, Nakauchi H, Hsieh P C. Circulating cells contribute to cardiomyocyte regeneration after injury. *Circ Res.* 2015; 116:633-641
26. Pajcini K V, Pomerantz J H, Alkan O, Doyonnas R, Blau H M. Myoblasts and macrophages share molecular components that contribute to cell-cell fusion. *J Cell Biol.* 2008; 180:1005-1019
27. Hochreiter-Hufford A E, Lee C S, Kinchen J M, Sokolowski J D, Arandjelovic S, Call J A, Klibanov A L, Yan Z, Mandell J W, Ravichandran K S. Phosphatidylserine receptor bai1 and apoptotic cells as new promoters of myoblast fusion. *Nature.* 2013; 497:263-267
28. Estrada J C, Tones Y, Benguria A, Dopazo A, Roche E, Carrera-Quintanar L, Perez R A, Enriquez J A, Torres R, Ramirez J C, Samper E, Bernad A. Human mesenchymal stem cell-replicative senescence and oxidative stress are closely linked to aneuploidy. *Cell death & disease.* 2013; 4:e691
29. Peterson S E, Westra J W, Rehen S K, Young H, Bushman D M, Paczkowski C M, Yung Y C, Lynch C L, Tran H T, Nickey K S, Wang Y C, Laurent L C, Loring J F, Carpenter M K, Chun J. Normal human pluripotent stem cell lines exhibit pervasive mosaic aneuploidy. *PLoS One.* 2011; 6:e23018
30. Boheler K R, Joodi R N, Qiao H, Juhasz O, Urick A L, Chuppa S L, Gundry R L, Wersto R P, Zhou R. Embryonic stem cell-derived cardiomyocyte heterogeneity and the isolation of immature and committed cells for cardiac remodeling and regeneration. *Stem Cells Int.* 2011; 2011: 214203
31. Pavlath G K, Blau H M. Expression of muscle genes in heterokaryons depends on gene dosage. *J Cell Biol.* 1986; 102:124-130
32. Islam M Q, Ringe J, Reichmann E, Migotti R, Sittinger M, da SML, Nardi N B, Magnusson P, Islam K. Functional characterization of cell hybrids generated by induced fusion of primary porcine mesenchymal stem cells with an immortal murine cell line. *Cell Tissue Res.* 2006; 326:123-137
33. Islam M Q, Panduri V, Islam K. Generation of somatic cell hybrids for the production of biologically active factors that stimulate proliferation of other cells. *Cell Prolif* 2007; 40:91-105
34. Foshay K M, Looney T J, Chari S, Mao F F, Lee J H, Zhang L, Fernandes C J, Baker S W, Clift K L, Gaetz J, Di C G, Xiang A P, Lahn B T. Embryonic stem cells induce pluripotency in somatic cell fusion through biphasic reprogramming. *Mol Cell.* 2012; 46:159-170
35. Dong F, Harvey J, Finan A, Weber K, Agarwal U, Penn M S. Myocardial cxcr4 expression is required for mesenchymal stem cell mediated repair following acute myocardial infarction. *Circulation.* 2012; 126:314-324
36. Taghavi S, Sharp T E, 3rd, Duran J M, Makarewich C A, Berretta R M, Starosta T, Kubo H, Barbe M, Houser S R. Autologous c-kit+ mesenchymal stem cell injections provide superior therapeutic benefit as compared to c-kit+ cardiac-derived stem cells in a feline model of isoproterenol-induced cardiomyopathy. *Clinical and translational science.* 2015
37. Poynter J A, Herrmann J L, Manukyan M C, Wang Y, Abarbanell A M, Weil B R, Brewster B D, Meldrum D R. Intracoronary mesenchymal stem cells promote postischemic myocardial functional recovery, decrease inflammation, and reduce apoptosis via a signal transducer and activator of transcription 3 mechanism. *Journal of the American College of Surgeons.* 2011; 213:253-260
38. Usunier B, Benderitter M, Tamarat R, Chapel A. Management of fibrosis: The mesenchymal stromal cells breakthrough. *Stem Cells Int.* 2014; 2014:340257
39. Yee K, Malliaras K, Kanazawa H, Tseliou E, Cheng K, Luthringer D J, Ho C S, Takayama K, Minamino N, Dawkins J F, Chowdhury S, Duong D T, Seinfeld J, Middleton R C, Dharmakumar R, Li D, Marban L, Makkar R R, Marban E. Allogeneic cardiospheres delivered via percutaneous transendocardial injection increase viable myocardium, decrease scar size, and attenuate cardiac dilatation in porcine ischemic cardiomyopathy. *PLoS One.* 2014; 9:e113805
40. Quijada P, Sussman M A. Making it stick: Chasing the optimal stem cells for cardiac regeneration. *Expert review of cardiovascular therapy.* 2014; 12:1275-1288
41. Chong J J, Yang X, Don C W, Minami E, Liu Y W, Weyers J J, Mahoney W M, Van Biber B, Cook S M, Palpant N J, Gantz J A, Fugate J A, Muskheli V, Gough G M, Vogel K W, Astley C A, Hotchkiss C E, Baldessari A, Pabon L, Reinecke H, Gill E A, Nelson V, Kiem H P, Laflamme M A, Murry C E. Human embryonic-stem-cell-derived cardiomyocytes regenerate non-human primate hearts. *Nature.* 2014; 510:273-277

42. Nauta A J, Fibbe W E. Immunomodulatory properties of mesenchymal stromal cells. *Blood.* 2007; 110:3499-3506

43. Tat P A, Sumer H, Pralong D, Verma P J. The efficiency of cell fusion-based reprogramming is affected by the somatic cell type and the in vitro age of somatic cells. *Cell Reprogram.* 2011; 13:331-344.

METHODS SECTION REFERENCES

1. Konstandin M H, Toko H, Gastelum G M, Quijada P, De La Torre A, Quintana M, Collins B, Din S, Avitabile D, Volkers M, Gude N, Fassler R, Sussman M A. Fibronectin is essential for reparative cardiac progenitor cell response after myocardial infarction. *Circ Res.* 2013; 113:115-125

2. Hariharan N, Quijada P, Mohsin S, Joyo A, Samse K, Monsanto M, De La Tone A, Avitabile D, Ormachea L, McGregor M J, Tsai E J, Sussman M A. Nucleostemin rejuvenates cardiac progenitor cells and antagonizes myocardial aging. *Journal of the American College of Cardiology.* 2015; 65:133-147

3. Tsujita Y, Muraski J, Shiraishi I, Kato T, Kajstura J, Anversa P, Sussman M A. Nuclear targeting of akt antagonizes aspects of cardiomyocyte hypertrophy. *Proc Natl Acad Sci USA.* 2006; 103:11946-11951

4. Muraski J A, Fischer K M, Wu W, Cottage C T, Quijada P, Mason M, Din S, Gude N, Alvarez R, Jr., Rota M, Kajstura J, Wang Z, Schaefer E, Chen X, MacDonnel S, Magnuson N, Houser S R, Anversa P, Sussman M A. Pim-1 kinase antagonizes aspects of myocardial hypertrophy and compensation to pathological pressure overload. *Proc Natl Acad Sci USA.* 2008; 105:13889-13894

5. Quijada P, Toko H, Fischer K M, Bailey B, Reilly P, Hunt K D, Gude N A, Avitabile D, Sussman M A. Preservation of myocardial structure is enhanced by pim-1 engineering of bone marrow cells. *Circ Res.* 2012; 111:77-86

Although the invention has been described in the context of certain embodiments, it is intended that the patent will not be limited to those embodiment; rather, the scope of this patent shall encompass the full lawful scope of the appended claims, and lawful equivalents thereof.

What is claimed is:

1. A method for making a chimeric cell, comprising:
   (a)
   (i) providing a first cell, wherein the first cell comprises:
      a cardiac stem cell of cardiac origin;
   (ii) providing a second cell, wherein the second cell comprises:
      (1) a mesenchymal progenitor cell or mesenchymal stem cell; or
      (2) an endothelial progenitor cell or endothelial stem cell;
   (iii) inducing fusion between the first cell and the second cell, thereby generating a cell fusion product.

2. The method of claim 1, further comprising clonally expanding the cell fusion product.

3. The method of claim 1, wherein the fusion is induced using a method comprising use of a cell fusion technique selected from the group consisting of: a Sendai virus or Hemagglutinating Virus of Japan Envelope (HVJ-E); a polyethylene glycol; liposomes or lipids; a fusion protein; and electrofusion.

4. The method of claim 1, wherein:
   the second cell is an endothelial progenitor cell or an endothelial stem cell.

5. The method of claim 1, wherein the first cell and the second cell are each a mammalian cell.

6. A cell fusion product or a viable chimera, produced by a method of claim 1.

7. A chromosomally-stable chimera cell line, produced by a method of claim 1.

8. A cell fusion product comprising: a fusion product of:
   a first cell comprising
      a cardiac progenitor cell (CPC);
      and
   a second cell comprising a stem cell or a progenitor cell.

9. The cell fusion product of claim 8, wherein said second cell comprises:
   (a) a mesenchymal stem cell of cardiac origin or non-cardiac origin;
   (b) an endothelial progenitor cell of cardiac origin or non-cardiac origin; or
   (c) a cardiac stem cell or a cardiac progenitor cell.

10. The cell fusion product of claim 8, wherein
    the second cell is a cardiac stem cell of cardiac origin.

11. A product of manufacture comprising a chimeric cell made by a method of claim 1,
    in combination with a delivery device suitable for delivering the chimeric cell to cardiac tissue.

12. The product of manufacture of claim 11,
    wherein the delivery device is an implant, a catheter, a stent, a gel, a hydrogel, a chitosan-based hydrogel, a biocompatible scaffold, or a biomimetic support.

13. A method for inducing cardiogenesis in a mammalian heart, comprising:

(a) providing a cell or a plurality of cells made by a method of claim 1, and
(b) introducing the cell or cells of (a) to a mammalian heart, thereby inducing cardiogenesis in the mammalian heart.

14. The method of claim 13, wherein the mammalian heart has an injury, a congenital defect, a genetic defect, or a dysfunction, and the method is effective to treat the injury, defect or the dysfunction.

15. A method for inducing cardiogenesis in a mammalian heart, comprising:
(a) providing a product of manufacture of claim 11, and
(b) introducing the product of manufacture of (a) to a mammalian heart, thereby inducing cardiogenesis in the mammalian heart.

16. A method for treating or ameliorating a heart injury subsequent to a myocardial infarction (MI), a congenital or genetic heart defect, or a heart dysfunction, comprising:
(a) providing a cell or a plurality of cells made by a method of claim 1, and
(b) administering the cell or cells of (a) to a heart of an individual in need thereof,
thereby treating or ameliorating the heart injury subsequent to a myocardial infarction (MI), congenital or genetic heart defect, or heart dysfunction or heart failure.

17. A method for treating or ameliorating a heart injury subsequent to a myocardial infarction (MI), a congenital or genetic heart defect, or a heart dysfunction, comprising:
(a) providing a cell fusion product of claim 8, and
(b) administering the cell fusion product of (a) to a heart of an individual in need thereof,
thereby treating or ameliorating the heart injury subsequent to a myocardial infarction (MI), congenital or genetic heart defect, or heart dysfunction or heart failure.

18. A method for treating or ameliorating a heart injury subsequent to a myocardial infarction (MI), a congenital or genetic heart defect, or a heart dysfunction, comprising:
(a) providing a product of manufacture of claim 11, and
(b) administering the product of manufacture of (a) to a heart of an individual in need thereof,
thereby treating or ameliorating the heart injury subsequent to a myocardial infarction (MI), congenital or genetic heart defect, or heart dysfunction or heart failure.

19. The method of claim 1, further comprising selecting a cell fusion product comprising a viable chimera of the first and the second cell.

20. The method of claim 2, further comprising selecting a chimera cell line on the basis of enhanced cardiogenic potential, reduced immunogenic potential, or both enhanced cardiogenic potential and reduced immunogenic potential.

21. The method of claim 5, wherein the cell fusion is a human cell to human cell fusion, a human cell to non-human cell fusion, or a non-human cell to a non-human cell fusion, or the cell fusion is a human, or a murine, a rodent, a rat or a mouse cell fusion product, or a murine to murine cell fusion product.

22. The product of manufacture of claim 11, fabricated as an implant, a catheter, a stent, or a medical device, or wherein the chimeric cell is formulated with or mixed with or within a gel, a hydrogel, a chitosan-based hydrogel, a biocompatible scaffold, or a biomimetic support.

23. The product of manufacture of claim 14, wherein the injury, defect or dysfunction is a myocardial infarction (MI), an ischemic injury, a heart failure, or results from a myocardial infarction (MI).

24. The method of claim 15, wherein the mammalian heart has an injury, a congenital or genetic defect, or a dysfunction, and the method is effective to treat the injury, defect or the dysfunction, or the injury, defect or dysfunction is a myocardial infarction (MI), an ischemic injury, a heart failure, or results from a myocardial infarction (MI).

\* \* \* \* \*